US012232821B2

United States Patent
McLaughlin et al.

(10) Patent No.: US 12,232,821 B2
(45) Date of Patent: Feb. 25, 2025

(54) NEEDLE GUIDANCE USING FIBER OPTIC SHAPE SENSING

(71) Applicant: Bard Access Systems, Inc., Salt Lake City, UT (US)

(72) Inventors: William Robert McLaughlin, Bountiful, UT (US); Steffan Sowards, Salt Lake City, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 227 days.

(21) Appl. No.: 17/569,350

(22) Filed: Jan. 5, 2022

(65) Prior Publication Data

US 2022/0211442 A1 Jul. 7, 2022

Related U.S. Application Data

(60) Provisional application No. 63/134,523, filed on Jan. 6, 2021.

(51) Int. Cl.
*A61B 34/20* (2016.01)
*A61B 17/34* (2006.01)
(Continued)

(52) U.S. Cl.
CPC .......... *A61B 34/20* (2016.02); *A61B 17/3403* (2013.01); *A61B 34/25* (2016.02);
(Continued)

(58) Field of Classification Search
CPC ..................... A61B 34/20; A61B 2034/2061
See application file for complete search history.

(56) References Cited

U.S. PATENT DOCUMENTS

| 4,813,429 A | 3/1989 | Eshel et al. |
| 5,099,845 A | 3/1992 | Besz et al. |

(Continued)

FOREIGN PATENT DOCUMENTS

| CN | 101132730 A | 2/2008 |
| CN | 111265309 A | 6/2020 |

(Continued)

OTHER PUBLICATIONS

EP 20853352.1 filed Mar. 7, 2022 Extended European Search Report dated Jul. 27, 2023.
(Continued)

*Primary Examiner* — Joseph M Santos Rodriguez
*Assistant Examiner* — Tommy T Ly
(74) *Attorney, Agent, or Firm* — Rutan & Tucker LLP

(57) ABSTRACT

Disclosed herein is a system, apparatus and method directed to placing a medical instrument in a patient body, where the system includes the medical instrument having a first optical fiber, a console and an interconnect having a second optical fiber to receive incident light from the console and propagate the incident light to the medical instrument. The interconnect includes a predetermined bend along its length, such that logic of the console may determine a positioning and an orientation of the medical instrument relative to the predetermined bend. Additionally, the logic may generate a display of the medical instrument based on the reflected light signals and the determination of the positioning and the orientation of the medical instrument relative to the predetermined bend, where the display may be rendered as an overlay on an ultrasound image.

19 Claims, 16 Drawing Sheets

(51) Int. Cl.
*A61B 34/00* (2016.01)
*A61B 90/00* (2016.01)

(52) U.S. Cl.
CPC .......... *A61B 2017/3405* (2013.01); *A61B 2017/3413* (2013.01); *A61B 2034/2061* (2016.02); *A61B 2090/378* (2016.02)

(56) References Cited

U.S. PATENT DOCUMENTS

| | | | |
|---|---|---|---|
| 5,163,935 A | 11/1992 | Black et al. | |
| 5,207,672 A | 5/1993 | Roth et al. | |
| 5,211,165 A | 5/1993 | Dumoulin et al. | |
| 5,275,151 A | 1/1994 | Shockey et al. | |
| 5,280,786 A | 1/1994 | Wlodarczyk et al. | |
| 5,423,321 A | 6/1995 | Fontenot | |
| 5,454,807 A | 10/1995 | Lennox et al. | |
| 5,460,182 A | 10/1995 | Goodman et al. | |
| 5,517,997 A | 5/1996 | Fontenot | |
| 5,622,170 A | 4/1997 | Schulz | |
| 5,740,808 A | 4/1998 | Panescu et al. | |
| 5,872,879 A | 2/1999 | Hamm | |
| 5,873,842 A | 2/1999 | Brennen et al. | |
| 5,879,306 A | 3/1999 | Fontenot et al. | |
| 5,906,579 A | 5/1999 | Vander Salm et al. | |
| 6,069,698 A | 5/2000 | Ozawa et al. | |
| 6,081,741 A | 6/2000 | Hollis | |
| 6,178,346 B1 | 1/2001 | Amundson et al. | |
| 6,208,887 B1 | 3/2001 | Clarke | |
| 6,319,227 B1 | 11/2001 | Mansouri-Ruiz | |
| 6,343,227 B1 | 1/2002 | Crowley | |
| 6,398,721 B1 | 6/2002 | Nakamura et al. | |
| 6,485,482 B1 | 11/2002 | Belef | |
| 6,564,089 B2 | 5/2003 | Izatt et al. | |
| 6,593,884 B1 | 7/2003 | Gilboa et al. | |
| 6,597,941 B2 | 7/2003 | Fontenot et al. | |
| 6,650,923 B1 | 11/2003 | Lesh et al. | |
| 6,673,214 B1 | 1/2004 | Marchitto et al. | |
| 6,685,666 B1 | 2/2004 | Fontenot | |
| 6,687,010 B1 | 2/2004 | Horii et al. | |
| 6,690,966 B1 | 2/2004 | Rava et al. | |
| 6,701,181 B2 | 3/2004 | Tang et al. | |
| 6,711,426 B2 | 3/2004 | Benaron et al. | |
| 6,816,743 B2 | 11/2004 | Moreno et al. | |
| 6,892,090 B2 | 5/2005 | Verard et al. | |
| 6,895,267 B2 | 5/2005 | Panescu et al. | |
| 7,132,645 B2 | 11/2006 | Kom | |
| 7,273,056 B2 | 9/2007 | Wilson et al. | |
| 7,344,533 B2 | 3/2008 | Pearson et al. | |
| 7,366,562 B2 | 4/2008 | Dukesherer et al. | |
| 7,366,563 B2 | 4/2008 | Kleen et al. | |
| 7,396,354 B2 | 7/2008 | Rychnovsky et al. | |
| 7,406,346 B2 | 7/2008 | Kleen et al. | |
| 7,515,265 B2 | 4/2009 | Alfano et al. | |
| 7,532,920 B1 | 5/2009 | Ainsworth et al. | |
| 7,587,236 B2 | 9/2009 | Demos et al. | |
| 7,603,166 B2 | 10/2009 | Casscells, III et al. | |
| 7,729,735 B1 | 6/2010 | Burchman | |
| 7,757,695 B2 | 7/2010 | Wilson et al. | |
| 7,758,499 B2 | 7/2010 | Adler | |
| 7,840,253 B2 | 11/2010 | Tremblay et al. | |
| 7,992,573 B2 | 8/2011 | Wilson et al. | |
| 8,032,200 B2 | 10/2011 | Tearney et al. | |
| 8,054,469 B2 | 11/2011 | Nakabayashi et al. | |
| 8,060,187 B2 | 11/2011 | Marshik-Geurts et al. | |
| 8,073,517 B1 | 12/2011 | Burchman | |
| 8,078,261 B2 | 12/2011 | Imam | |
| 8,187,189 B2 | 5/2012 | Jung et al. | |
| 8,267,932 B2 | 9/2012 | Baxter et al. | |
| 8,369,932 B2 | 2/2013 | Cinbis et al. | |
| 8,388,541 B2 | 3/2013 | Messerly et al. | |
| 8,571,640 B2 | 10/2013 | Holman | |
| 8,597,315 B2 | 12/2013 | Snow et al. | |
| 8,700,358 B1 | 4/2014 | Parker, Jr. | |
| 8,781,555 B2 | 7/2014 | Burnside et al. | |
| 8,798,721 B2 | 8/2014 | Dib | |
| 8,968,331 B1 | 3/2015 | Sochor | |
| 8,979,871 B2 | 3/2015 | Tyc et al. | |
| 9,060,687 B2 | 6/2015 | Yamanaka et al. | |
| 9,114,226 B1 | 8/2015 | Lash et al. | |
| 9,206,309 B2 | 12/2015 | Appleby et al. | |
| 9,360,630 B2 | 6/2016 | Jenner et al. | |
| 9,504,392 B2 | 11/2016 | Caron et al. | |
| 9,560,954 B2 | 2/2017 | Jacobs et al. | |
| 9,622,706 B2 | 4/2017 | Dick et al. | |
| 9,678,275 B1 | 6/2017 | Griffin | |
| 10,231,753 B2 | 3/2019 | Burnside et al. | |
| 10,258,240 B1 | 4/2019 | Eberle et al. | |
| 10,327,830 B2 | 6/2019 | Grant et al. | |
| 10,349,890 B2 | 7/2019 | Misener et al. | |
| 10,492,876 B2 | 12/2019 | Anastassiou et al. | |
| 10,568,586 B2 | 2/2020 | Begin et al. | |
| 10,631,718 B2 | 4/2020 | Petroff et al. | |
| 10,992,078 B2 | 4/2021 | Thompson et al. | |
| 11,123,047 B2 | 9/2021 | Jaffer et al. | |
| 11,525,670 B2 | 12/2022 | Messerly et al. | |
| 2002/0198457 A1 | 12/2002 | Tearney et al. | |
| 2003/0092995 A1 | 5/2003 | Thompson | |
| 2004/0129555 A1 | 7/2004 | Marchitto et al. | |
| 2004/0161362 A1 | 8/2004 | Bogert | |
| 2004/0242995 A1 | 12/2004 | Maschke | |
| 2005/0033264 A1 | 2/2005 | Redinger | |
| 2005/0163424 A1 | 7/2005 | Chen | |
| 2005/0261598 A1 | 11/2005 | Banet et al. | |
| 2005/0278010 A1 | 12/2005 | Richardson | |
| 2006/0013523 A1 | 1/2006 | Childlers et al. | |
| 2006/0015136 A1 | 1/2006 | Besselink | |
| 2006/0036164 A1 | 2/2006 | Wilson et al. | |
| 2006/0189959 A1 | 8/2006 | Schneiter | |
| 2006/0200049 A1 | 9/2006 | Leo et al. | |
| 2006/0241395 A1 | 10/2006 | Kruger et al. | |
| 2006/0241492 A1 | 10/2006 | Boese et al. | |
| 2007/0156019 A1 | 7/2007 | Arkin et al. | |
| 2007/0201793 A1 | 8/2007 | Askins et al. | |
| 2007/0287886 A1 | 12/2007 | Saadat | |
| 2007/0287934 A1 | 12/2007 | Babaev | |
| 2007/0299425 A1 | 12/2007 | Waner et al. | |
| 2008/0039715 A1 | 2/2008 | Wilson et al. | |
| 2008/0082004 A1 | 4/2008 | Banet et al. | |
| 2008/0172119 A1 | 7/2008 | Yamasaki et al. | |
| 2008/0183128 A1 | 7/2008 | Morriss et al. | |
| 2008/0212082 A1 | 9/2008 | Froggatt et al. | |
| 2008/0285909 A1 | 11/2008 | Younge et al. | |
| 2008/0319290 A1 | 12/2008 | Mao et al. | |
| 2009/0054908 A1 | 2/2009 | Zand et al. | |
| 2009/0062634 A1 | 3/2009 | Say et al. | |
| 2009/0118612 A1 | 5/2009 | Grunwald et al. | |
| 2009/0137952 A1 | 5/2009 | Ramamurthy et al. | |
| 2009/0234328 A1 | 9/2009 | Cox et al. | |
| 2009/0304582 A1 | 12/2009 | Rousso et al. | |
| 2009/0314925 A1 | 12/2009 | Van Vorhis et al. | |
| 2010/0016729 A1 | 1/2010 | Futrell | |
| 2010/0030063 A1 | 2/2010 | Lee et al. | |
| 2010/0030132 A1 | 2/2010 | Niezgoda et al. | |
| 2010/0063534 A1 | 3/2010 | Kugler et al. | |
| 2010/0114115 A1 | 5/2010 | Schlesinger et al. | |
| 2010/0286531 A1 | 11/2010 | Ryan et al. | |
| 2010/0312095 A1 | 12/2010 | Jenkins et al. | |
| 2011/0060229 A1 | 3/2011 | Hulvershorn et al. | |
| 2011/0144481 A1 | 6/2011 | Feer et al. | |
| 2011/0166442 A1 | 7/2011 | Sarvazyan | |
| 2011/0172591 A1 | 7/2011 | Babaev | |
| 2011/0172680 A1 | 7/2011 | Younge et al. | |
| 2011/0237958 A1 | 9/2011 | Onimura | |
| 2011/0242532 A1 | 10/2011 | McKenna | |
| 2011/0245662 A1 | 10/2011 | Eggers et al. | |
| 2011/0288405 A1 | 11/2011 | Razavi et al. | |
| 2011/0295108 A1 | 12/2011 | Cox et al. | |
| 2011/0313280 A1 | 12/2011 | Govari et al. | |
| 2012/0046562 A1 | 2/2012 | Powers et al. | |
| 2012/0065481 A1 | 3/2012 | Hunter et al. | |
| 2012/0101413 A1 | 4/2012 | Beetel et al. | |
| 2012/0136242 A1 | 5/2012 | Qi et al. | |
| 2012/0143029 A1 | 6/2012 | Silverstein et al. | |
| 2012/0184827 A1 | 7/2012 | Shwartz et al. | |

(56) References Cited

U.S. PATENT DOCUMENTS

| | | | |
|---|---|---|---|
| 2012/0184955 A1 | 7/2012 | Pivotto et al. | |
| 2012/0289783 A1 | 11/2012 | Duindam et al. | |
| 2012/0321243 A1* | 12/2012 | Younge | A61B 1/009 385/13 |
| 2013/0028554 A1 | 1/2013 | Wong et al. | |
| 2013/0072943 A1 | 3/2013 | Parmar | |
| 2013/0096482 A1 | 4/2013 | Bertrand et al. | |
| 2013/0104884 A1 | 5/2013 | Vazales et al. | |
| 2013/0188855 A1 | 7/2013 | Desjardins et al. | |
| 2013/0204124 A1 | 8/2013 | Duindam et al. | |
| 2013/0211246 A1 | 8/2013 | Parasher | |
| 2013/0296693 A1 | 11/2013 | Wenzel et al. | |
| 2013/0310668 A1 | 11/2013 | Young | |
| 2013/0317372 A1 | 11/2013 | Eberle et al. | |
| 2013/0324840 A1 | 12/2013 | Zhongping et al. | |
| 2014/0121468 A1 | 5/2014 | Eichenholz | |
| 2014/0221829 A1 | 8/2014 | Maitland et al. | |
| 2014/0275997 A1 | 9/2014 | Chopra et al. | |
| 2015/0029511 A1 | 1/2015 | Hooft et al. | |
| 2015/0031987 A1 | 1/2015 | Pameijer et al. | |
| 2015/0080688 A1 | 3/2015 | Cinbis et al. | |
| 2015/0099979 A1 | 4/2015 | Caves et al. | |
| 2015/0119700 A1 | 4/2015 | Liang et al. | |
| 2015/0141854 A1 | 5/2015 | Eberle et al. | |
| 2015/0164571 A1 | 6/2015 | Saadat | |
| 2015/0190221 A1 | 7/2015 | Schaefer et al. | |
| 2015/0209113 A1 | 7/2015 | Burkholz et al. | |
| 2015/0209117 A1 | 7/2015 | Flexman et al. | |
| 2015/0254526 A1 | 9/2015 | Denissen | |
| 2015/0320977 A1 | 11/2015 | Vitullo et al. | |
| 2016/0018602 A1 | 1/2016 | Govari et al. | |
| 2016/0067449 A1 | 3/2016 | Misener et al. | |
| 2016/0102969 A1* | 4/2016 | Verstege | A61B 1/009 250/206 |
| 2016/0166326 A1 | 6/2016 | Bakker et al. | |
| 2016/0166341 A1 | 6/2016 | Iordachita et al. | |
| 2016/0184020 A1 | 6/2016 | Kowalewski et al. | |
| 2016/0213432 A1 | 7/2016 | Flexman et al. | |
| 2016/0354038 A1 | 12/2016 | Demirtas et al. | |
| 2017/0020394 A1 | 1/2017 | Harrington | |
| 2017/0079681 A1 | 3/2017 | Burnside et al. | |
| 2017/0082806 A1 | 3/2017 | Van Der Mark et al. | |
| 2017/0173349 A1 | 6/2017 | Pfleiderer et al. | |
| 2017/0196479 A1 | 7/2017 | Liu et al. | |
| 2017/0201036 A1 | 7/2017 | Cohen et al. | |
| 2017/0215973 A1 | 8/2017 | Flexman et al. | |
| 2017/0231699 A1 | 8/2017 | Flexman et al. | |
| 2017/0273542 A1 | 9/2017 | Au | |
| 2017/0273565 A1 | 9/2017 | Ma et al. | |
| 2017/0273628 A1 | 9/2017 | Ofek et al. | |
| 2017/0290563 A1* | 10/2017 | Cole | A61M 25/0147 |
| 2017/0311901 A1 | 11/2017 | Zhao et al. | |
| 2017/0319279 A1 | 11/2017 | Fish et al. | |
| 2018/0008443 A1 | 1/2018 | Cole et al. | |
| 2018/0031493 A1 | 2/2018 | Tojo et al. | |
| 2018/0095231 A1 | 4/2018 | Lowell et al. | |
| 2018/0113038 A1 | 4/2018 | Janabi-Sharifi et al. | |
| 2018/0116551 A1 | 5/2018 | Newman et al. | |
| 2018/0140170 A1 | 5/2018 | Van Putten et al. | |
| 2018/0235709 A1 | 8/2018 | Donhowe et al. | |
| 2018/0239124 A1 | 8/2018 | Naruse et al. | |
| 2018/0240237 A1 | 8/2018 | Donhowe et al. | |
| 2018/0250088 A1 | 9/2018 | Brennan et al. | |
| 2018/0264227 A1 | 9/2018 | Flexman et al. | |
| 2018/0279909 A1 | 10/2018 | Noonan et al. | |
| 2018/0289390 A1 | 10/2018 | Amorizzo et al. | |
| 2018/0289927 A1 | 10/2018 | Messerly | |
| 2018/0339134 A1 | 11/2018 | Leo | |
| 2018/0360545 A1 | 12/2018 | Cole et al. | |
| 2019/0059743 A1 | 2/2019 | Ramachandran et al. | |
| 2019/0110844 A1 | 4/2019 | Misener et al. | |
| 2019/0231272 A1 | 8/2019 | Yamaji | |
| 2019/0237902 A1 | 8/2019 | Thompson et al. | |
| 2019/0247132 A1 | 8/2019 | Harks et al. | |
| 2019/0307331 A1 | 10/2019 | Saadat et al. | |
| 2019/0321110 A1 | 10/2019 | Grunwald et al. | |
| 2019/0343424 A1 | 11/2019 | Blumenkranz et al. | |
| 2019/0343702 A1 | 11/2019 | Smith | |
| 2019/0357875 A1 | 11/2019 | Qi et al. | |
| 2019/0374130 A1 | 12/2019 | Bydlon et al. | |
| 2020/0030575 A1 | 1/2020 | Bogusky et al. | |
| 2020/0046434 A1 | 2/2020 | Graetzel et al. | |
| 2020/0054399 A1 | 2/2020 | Duindam et al. | |
| 2020/0188036 A1 | 6/2020 | Ding et al. | |
| 2020/0305983 A1 | 10/2020 | Yampolsky et al. | |
| 2020/0315770 A1 | 10/2020 | Dupont et al. | |
| 2020/0394789 A1 | 12/2020 | Freund et al. | |
| 2021/0015470 A1* | 1/2021 | Prisco | A61B 34/35 |
| 2021/0023341 A1 | 1/2021 | Decheek et al. | |
| 2021/0045814 A1 | 2/2021 | Thompson et al. | |
| 2021/0068911 A1 | 3/2021 | Walker et al. | |
| 2021/0298680 A1 | 3/2021 | Sowards et al. | |
| 2021/0244311 A1 | 8/2021 | Zhao et al. | |
| 2021/0268229 A1 | 9/2021 | Sowards et al. | |
| 2021/0271035 A1 | 9/2021 | Sowards et al. | |
| 2021/0275257 A1 | 9/2021 | Prior et al. | |
| 2021/0330399 A1 | 10/2021 | Netravali et al. | |
| 2021/0401456 A1 | 12/2021 | Cox et al. | |
| 2021/0401509 A1 | 12/2021 | Misener et al. | |
| 2021/0402144 A1 | 12/2021 | Messerly | |
| 2022/0011192 A1 | 1/2022 | Misener et al. | |
| 2022/0034733 A1 | 2/2022 | Misener et al. | |
| 2022/0096796 A1 | 3/2022 | McLaughlin et al. | |
| 2022/0110695 A1 | 4/2022 | Sowards et al. | |
| 2022/0151568 A1 | 5/2022 | Yao et al. | |
| 2022/0152349 A1 | 5/2022 | Sowards et al. | |
| 2022/0160209 A1 | 5/2022 | Sowards et al. | |
| 2022/0172354 A1 | 6/2022 | Misener et al. | |
| 2022/0233246 A1 | 7/2022 | Visener et al. | |
| 2022/0369934 A1 | 11/2022 | Sowards et al. | |
| 2023/0081198 A1 | 3/2023 | Sowards et al. | |
| 2023/0097431 A1 | 3/2023 | Sowards et al. | |
| 2023/0101030 A1 | 3/2023 | Misener et al. | |
| 2023/0108604 A1 | 4/2023 | Messerly et al. | |
| 2023/0126813 A1 | 4/2023 | Sowards et al. | |
| 2023/0243715 A1 | 8/2023 | Misener et al. | |
| 2023/0248444 A1 | 8/2023 | Misener et al. | |
| 2023/0251150 A1 | 8/2023 | Misener et al. | |
| 2023/0337985 A1 | 10/2023 | Sowards et al. | |
| 2023/0414112 A1 | 12/2023 | Misener et al. | |
| 2024/0000515 A1 | 1/2024 | Misener et al. | |
| 2024/0050708 A1 | 2/2024 | Misener | |
| 2024/0099659 A1 | 3/2024 | Sowards et al. | |
| 2024/0108856 A1 | 4/2024 | Messerly | |
| 2024/0216077 A1 | 7/2024 | Thompson et al. | |
| 2024/0335237 A1 | 10/2024 | Sowards et al. | |

FOREIGN PATENT DOCUMENTS

| | | |
|---|---|---|
| CN | 113080937 A | 7/2021 |
| DE | 102016109601 A1 | 11/2017 |
| EP | 2240111 A2 | 10/2010 |
| EP | 2907445 A1 | 8/2015 |
| EP | 3545849 A1 | 10/2019 |
| EP | 3705020 A1 | 9/2020 |
| JP | 7366562 B2 | 10/2023 |
| KR | 20190098512 A | 8/2019 |
| WO | 99/64099 A1 | 12/1999 |
| WO | 1999064099 A1 | 12/1999 |
| WO | 2006113394 A2 | 10/2006 |
| WO | 2006122001 A2 | 11/2006 |
| WO | 2007002323 A2 | 1/2007 |
| WO | 2009/155325 A2 | 12/2009 |
| WO | 2011121516 A2 | 10/2011 |
| WO | 2011141830 A1 | 11/2011 |
| WO | 2011150376 A1 | 12/2011 |
| WO | 2012064769 A2 | 5/2012 |
| WO | 2015044930 A1 | 4/2015 |
| WO | 2015074045 A2 | 5/2015 |
| WO | 2016038492 A1 | 3/2016 |
| WO | 2016/061431 A1 | 4/2016 |
| WO | 2016051302 A1 | 4/2016 |
| WO | 2016149819 A1 | 9/2016 |
| WO | 2018/096491 A1 | 5/2018 |

(56) References Cited

FOREIGN PATENT DOCUMENTS

| | | |
|---|---|---|
| WO | 2019037071 A1 | 2/2019 |
| WO | 2019/046769 A1 | 3/2019 |
| WO | 2019070423 A1 | 4/2019 |
| WO | 2019230713 A1 | 12/2019 |
| WO | 2020/182997 A1 | 9/2020 |
| WO | 2021030092 A1 | 2/2021 |
| WO | 2021108688 A1 | 6/2021 |
| WO | 2021108697 A1 | 6/2021 |
| WO | 2021/138096 A1 | 7/2021 |
| WO | 2021216089 A1 | 10/2021 |
| WO | 2022/031613 A1 | 2/2022 |
| WO | 2022/081723 A1 | 4/2022 |
| WO | 2022150411 A1 | 7/2022 |
| WO | 2022/164902 A1 | 8/2022 |
| WO | 2022/245987 A1 | 11/2022 |
| WO | 2023043954 A1 | 3/2023 |
| WO | 2023049443 A1 | 3/2023 |
| WO | 2023055810 A1 | 4/2023 |
| WO | 2023076143 A1 | 5/2023 |
| WO | 2023211752 A1 | 11/2023 |
| WO | 2024006384 A1 | 1/2024 |
| WO | 2024006441 A1 | 1/2024 |
| WO | 2024064334 A1 | 3/2024 |

OTHER PUBLICATIONS

PCT/US2023/019239 filed Apr. 20, 2023 International Search Report and Written Opinion dated Jul. 20, 2023.

U.S. Appl. No. 16/984,104, filed Aug. 3, 2020 Non-Final Office Action dated Jun. 22, 2023.

U.S. Appl. No. 17/105,310, filed Nov. 25, 2020 Notice of Allowance dated Aug. 2, 2023.

U.S. Appl. No. 17/357,186, filed Jun. 24, 2021 Notice of Allowance dated Aug. 23, 2023.

Fiber Optic RealShape (FORS) technology—research. Philips. (Oct. 18, 2018). Retrieved Feb. 28, 2023, from https://www.philips.com/a-w/research/research-programs/fors.html (Year: 2018).

U.S. Appl. No. 16/984,104, filed Aug. 3, 2020 Restriction Requirement dated Mar. 13, 2023.

U.S. Appl. No. 17/357,186, filed Jun. 24, 2021 Non Final Office Action dated May 30, 2023.

U.S. Appl. No. 17/500,678, filed Oct. 13, 2021 Non-Final Office Action dated Mar. 15, 2023.

PCT/US2020/062396 filed Nov. 25, 2020 International Preliminary Report on Patentability dated Jan. 29, 2021.

PCT/US2020/062407 filed Nov. 25, 2020 International Preliminary Report on Patentability dated Jan. 25, 2021.

PCT/US2022/011347 filed Jan. 5, 2022 International Search Report and Written Opinion dated May 3, 2022.

PCT/US2022/013897 filed Jan. 26, 2022 International Search Report and Written Opinion dated May 11, 2022.

U.S. Appl. No. 15/947,267, filed Apr. 6, 2018 Final Office Action dated Apr. 22, 2022.

PCT/US2022/029894 filed May 18, 2022, International Search Report and Written Opinion dated Sep. 1, 2022.

U.S. Appl. No. 17/105,259, filed Nov. 25, 2020, Notice of Allowance dated Jul. 20, 2022.

U.S. Appl. No. 17/357,561, filed Jun. 24, 2021 Non-Final Office Action dated Aug. 11, 2022.

U.S. Appl. No. 17/371,993, filed Jul. 9, 2021 Non-Final Office Action dated Jul. 12, 2022.

U.S. Appl. No. 17/392,002, filed Aug. 2, 2021 Non-Final Office Action dated Sep. 12, 2022.

Dziuda L et al: "Monitoring Respiration and Cardiac Activity Using Fiber Bragg Grating-Based Sensor", IEEE Transactions On Biomedical Engineering vol. 59, No. 7, Jul. 2012 pp. 1934-1942.

Dziuda L. et al: "Fiber-optic sensor for monitoring respiration and cardiac activity", 2011 IEEE Sensors Proceedings : Limerick, Ireland, Oct. 2011 pp. 413-416.

EP 20893677.3 filed Jun. 22, 2022 Extended European Search Report dated Oct. 13, 2023.

EP 20894633.5 filed Jun. 22, 2022 Extended European Search Report dated Oct. 16, 2023.

PCT/US2021/052046 filed Sep. 24, 2021 International Search Report and Written Opinion dated Jan. 11, 2022.

PCT/US2023/026487 filed Jun. 28, 2023 International Search Report and Written Opinion dated Sep. 6, 2023.

PCT/US2023/026581 filed Jun. 29, 2023 International Search Report and Written Opinion dated Oct. 27, 2023.

U.S. Appl. No. 16/984,104, filed Aug. 3, 2020 Final Office Action dated Sep. 21, 2023.

U.S. Appl. No. 16/984,104, filed Aug. 3, 2020 Notice of Allowance dated Nov. 21, 2023.

U.S. Appl. No. 17/484,960, filed Sep. 24, 2021 Non-Final Office Action dated Oct. 5, 2023.

U.S. Appl. No. 17/500,678, filed Oct. 13, 2021 Final Office Action dated Sep. 21, 2023.

Jackle Sonja et al. "Three-dimensional guidance including shape sensing of a stentgraft system for endovascular aneurysm repair." International Journal of Computer Assisted Radiology and Surgery, Springer DE. vol. 15, No. 6, May 7, 2020.

PCT/US2022/043706 filed Sep. 16, 2022 International Search Report and Written Opinion dated Nov. 24, 2022.

PCT/US2022/044696 filed Sep. 26, 2022 International Search Report and Written Opinion dated Jan. 23, 2023.

PCT/US2022/045051 filed Sep. 28, 2022 International Search Report and Written Opinion dated Jan. 2, 2023.

PCT/US2022/047538 filed Oct. 24, 2022 International Search Report and Written Opinion dated Jan. 26, 2023.

U.S. Appl. No. 15/947,267, filed Apr. 6, 2018 Examiner's Answer dated Novemeber 28, 2022.

U.S. Appl. No. 17/105,310, filed Nov. 25, 2020 Non-Final Office Action dated Feb. 22, 2023.

U.S. Appl. No. 17/357,186, filed Jun. 24, 2021 Restriction Requirement dated Mar. 7, 2023.

U.S. Appl. No. 17/357,561, filed Jun. 24, 2021 Notice of Allowance dated Dec. 9, 2022.

U.S. Appl. No. 17/371,993, filed Jul. 9, 2021 Notice of Allowance dated Nov. 3, 2022.

U.S. Appl. No. 17/392,002, filed Aug. 2, 2021, Corrected Notice of Allowability dated Feb. 23, 2023.

U.S. Appl. No. 17/392,002, filed Aug. 2, 2021, Notice of Allowance dated Jan. 19, 2023.

PCT/US2018/026493 filed Apr. 6, 2018 International Search Report and Written Opinion dated Jun. 22, 2018.

PCT/US2020/044801 filed Aug. 3, 2020 International Search Report and Written Opinion dated Oct. 26, 2020.

PCT/US2020/062396 filed Nov. 25, 2020 International Search Report and Written Opinion dated Mar. 2, 2021.

PCT/US2020/062407 filed Nov. 25, 2020 International Search Report and Written Opinion dated Mar. 11, 2021.

PCT/US2021/019713 filed Feb. 25, 2021 International Search Report and Written Opinion dated Jul. 6, 2021.

PCT/US2021/020079 filed Feb. 26, 2021 International Search Report and Written Opinion dated Jun. 4, 2021.

PCT/US2021/020732 filed Mar. 3, 2021 International Search Report and Written Opinion dated Jul. 5, 2021.

PCT/US2021/038899 filed Jun. 24, 2021 International Search Report and Written Opinion dated Oct. 6, 2021.

PCT/US2021/038954 filed Jun. 24, 2021 International Search Report and Written Opinion dated Oct. 28, 2021.

PCT/US2021/041128 filed Jul. 9, 2021 International Search Report and Written Opinion dated Oct. 25, 2021.

PCT/US2021/044216 filed Aug. 2, 2021 International Search Report and Written Opinion dated Nov. 18, 2021.

PCT/US2021/054802 filed Oct. 13, 2021 International Search Report and Written Opinion dated Feb. 2, 2022.

PCT/US2021/060849 filed Nov. 24, 2021 International Search Report and Written Opinion dated Mar. 9, 2022.

U.S. Appl. No. 15/947,267, filed Apr. 6, 2018 Final Office Action dated Jun. 30, 2021.

(56) References Cited

OTHER PUBLICATIONS

U.S. Appl. No. 15/947,267, filed Apr. 6, 2018 Final Office Action dated Nov. 10, 2020.
U.S. Appl. No. 15/947,267, filed Apr. 6, 2018 Non-Final Office Action dated Mar. 12, 2021.
U.S. Appl. No. 15/947,267, filed Apr. 6, 2018 Non-Final Office Action dated May 29, 2020.
U.S. Appl. No. 15/947,267, filed Apr. 6, 2018 Non-Final Office Action dated Oct. 13, 2021.
U.S. Appl. No. 17/185,777, filed Feb. 25, 2021 Non-Final Office Action dated Feb. 9, 2022.
PCT/US2023/033471 filed Sep. 22, 2023 International Search Report and Written Opinion dated Dec. 21, 2023.
U.S. Appl. No. 17/500,678, filed Oct. 13, 2021 Advisory Action dated Dec. 7, 2023.
U.S. Appl. No. 17/500,678, filed Oct. 13, 2021 Non-Final Office Action dated Jan. 19, 2024.
U.S. Appl. No. 18/079,653, filed Dec. 12, 2022 Non-Final Office Action dated Feb. 6, 2024.
U.S. Appl. No. 18/135,337, filed Apr. 17, 2023 Non-Final Office Action dated Dec. 22, 2023.
U.S. Appl. No. 18/135,337, filed Apr. 17, 2023 Notice of Allowance dated Mar. 8, 2024.
U.S. Appl. No. 17/484,960, filed Sep. 24, 2021 Notice of Allowance dated Apr. 12, 2024.
U.S. Appl. No. 17/747,903, filed May 18, 2022 Restriction Requirement dated May 28, 2024.
U.S. Appl. No. 17/955,019, filed Sep. 28, 2022 Restriction Requirement dated Jun. 6, 2024.
U.S. Appl. No. 18/079,653, filed Dec. 12, 2022 Notice of Allowance dated Jun. 4, 2024.
U.S. Appl. No. 18/132,623, filed Apr. 10, 2023, Non-Final Office Action dated May 3, 2024.
U.S. Appl. No. 17/971,873, filed Oct. 24, 2022 Non-Final Office Action dated Jun. 6, 2024.
Mayoral et al. Fiber Optic Sensors for Vital Signs Monitoring. A Review of Its Practicality in the Health Field. Biosensors (Basel). Feb. 23, 2021;11(2):58. doi: 10.3390/bios11020058.
U.S. Appl. No. 15/947,267, filed Apr. 6, 2018 Notice of Allowance dated Jul. 16, 2024.
U.S. Appl. No. 17/500,678, filed Oct. 13, 2021 Final Office Action dated Aug. 27, 2024.
U.S. Appl. No. 17/728,802, filed Apr. 25, 2022 Non-Final Office Action dated Aug. 28, 2024.
U.S. Appl. No. 17/747,903, filed May 18, 2022 Non-Final Office Action dated Aug. 15, 2024.
U.S. Appl. No. 17/852,138, filed Jun. 28, 2022 Non-Final Office Action dated Sep. 18, 2024.
U.S. Appl. No. 17/853,590, filed Jun. 29, 2022 Non-Final Office Action dated Oct. 17, 2024.
U.S. Appl. No. 17/955,019, filed Sep. 28, 2022 Non-Final Office Action dated Sep. 27, 2024.
U.S. Appl. No. 18/132,231, filed Apr. 7, 2023 Non-Final Office Action dated Jul. 12, 2024.
U.S. Appl. No. 18/132,623, filed Apr. 10, 2023, Final Office Action dated Sep. 6, 2024.
U.S. Appl. No. 18/538,111, filed Dec. 13, 2023 Non-Final Office Action dated Aug. 9, 2024.
U.S. Appl. No. 18/607,144, filed Mar. 15, 2024 Non-Final Office Action dated Sep. 24, 2024.

* cited by examiner

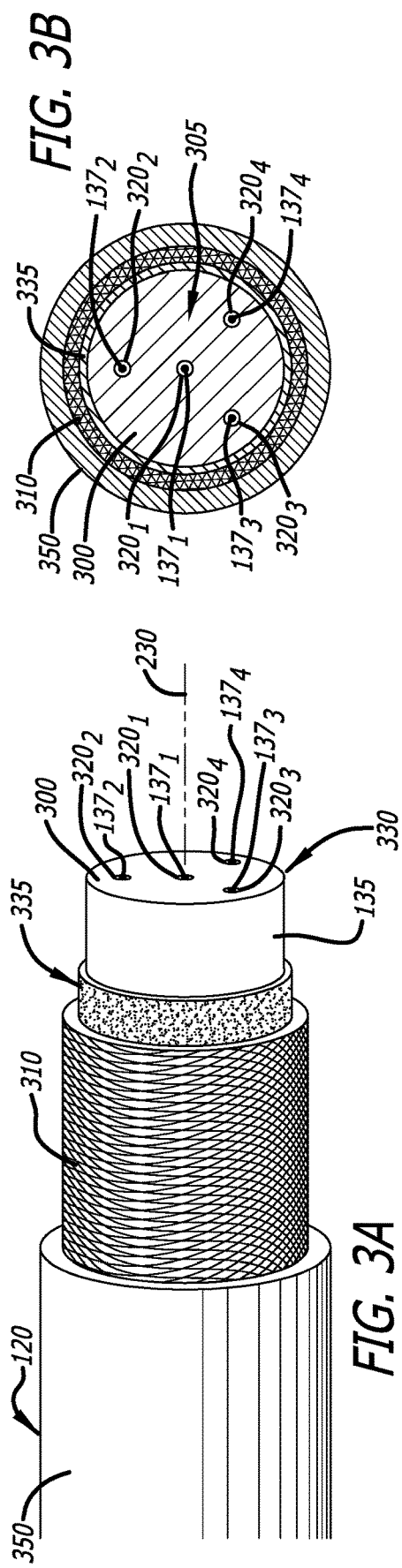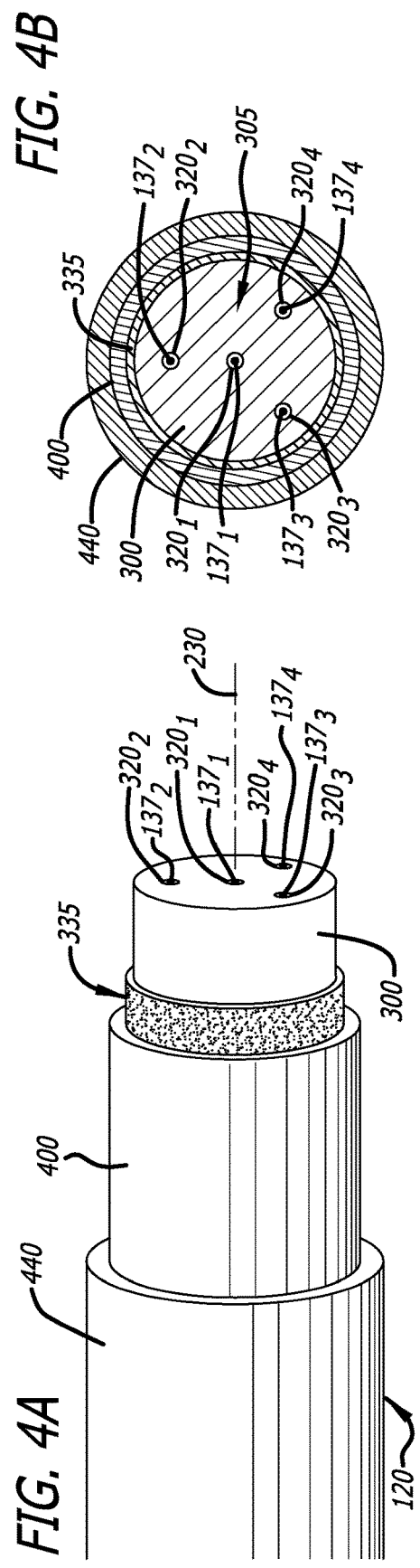

NEEDLE GUIDANCE USING FIBER OPTIC SHAPE SENSING

PRIORITY

This application claims the benefit of priority to U.S. Provisional Application No. 63/134,523, filed Jan. 6, 2021, which is incorporated by reference in its entirety into this application.

BACKGROUND

In the past, certain intravascular guidance of medical instruments, such as guidewires and catheters for example, have used fluoroscopic methods for tracking tips of the medical instruments and determining whether distal tips are appropriately localized in their target anatomical structures. However, such fluoroscopic methods expose patients and their attending clinicians to harmful X-ray radiation. Moreover, in some cases, the patients are exposed to potentially harmful contrast media needed for the fluoroscopic methods.

More recently, electromagnetic tracking systems have been used involving stylets. Generally, electromagnetic tracking systems feature three components: a field generator, a sensor unit and control unit. The field generator uses several coils to generate a position-varying magnetic field, which is used to establish a coordinate space. Attached to the stylet, such as near a distal end (tip) of the stylet for example, the sensor unit includes small coils in which current is induced via the magnetic field. Based on the electrical properties of each coil, the position and orientation of the medical instrument may be determined within the coordinate space. The control unit controls the field generator and captures data from the sensor unit.

Although electromagnetic tracking systems avoid line-of-sight reliance in tracking the tip of a stylet while obviating radiation exposure and potentially harmful contrast media associated with fluoroscopic methods, electromagnetic tracking systems are prone to interference. More specifically, since electromagnetic tracking systems depend on the measurement of magnetic fields produced by the field generator, these systems are subject to electromagnetic field interference, which may be caused by the presence of many different types of consumer electronics such as cellular telephones. Additionally, electromagnetic tracking systems are subject to signal drop out, depend on an external sensor, and are defined to a limited depth range.

Disclosed herein is a system including a medical instrument monitoring system including a medical instrument having disposed therein an optical fiber and methods performed thereby where the system is configured to provide tracking information of a distal tip of the medical instrument using optical fiber technology to assist a clinician in inserting the medical instrument within a patient vasculature. In some embodiments, an optical fiber may be coupled to the medical instrument and to a console, where the optical fiber includes a known bend or kink, which may serve as a point of reference when determining a positioning or orientation of the medical instrument. In some embodiments, the optical fiber may be coupled to an ultrasound probe such that the known bend or kink is disposed at the coupling point. In other embodiments, the optical fiber may be coupled to the patient such that the known bend or kink is disposed at the coupling point. Further, some embodiments combine the fiber optic shape sensing functionality with one or more of intravascular electrocardiogram (ECG) monitoring, impedance/conductance sensing and blood flow directional detection.

SUMMARY

Briefly summarized, embodiments disclosed herein are directed to systems, apparatus and methods for providing tracking information of a distal tip of the medical instrument using optical fiber technology. In some embodiments, the medical instrument includes an optical fiber having one or more optical fiber cores, where each are configured with an array of sensors (reflective gratings), which are spatially distributed over a prescribed length of the core fiber to generally sense external strain and temperature on those regions of the core fiber occupied by the sensor. Each optical fiber core is configured to receive light (e.g., broadband) from a console during advancement through the vasculature of a patient, where the broadband light propagates along at least a partial distance of the optical fiber core toward the distal end. Given that each sensor positioned along the optical fiber core is configured to reflect light of a different, specific spectral width, the array of sensors enables distributed measurements throughout the prescribed length of the medical instrument. These distributed measurements may include wavelength shifts having a correlation with strain and/or temperature experienced by the sensor.

The reflected light from the sensors (reflective gratings) within an optical fiber core is returned from the medical instrument for processing by the console. The physical state of the medical instrument may be ascertained based on analytics of the wavelength shifts of the reflected light. For example, the strain caused through bending of the medical instrument and hence angular modification of the optical fiber core, causes different degrees of deformation. The different degrees of deformation alter the shape of the sensors (reflective grating) positioned on the optical fiber core, which may cause variations (shifts) in the wavelength of the reflected light from the sensors positioned on the optical fiber core. The optical fiber core may comprise a single optical fiber, or a plurality of optical fibers (in which case, the optical fiber core is referred to as a "multi-core optical fiber").

As used herein, the term "core fiber," generally refers to a single optical fiber core disposed within a medical instrument. Thus, discussion of a core fiber refers to single optical fiber core and discussion of a multi-core optical fiber refers to a plurality of core fibers. Various embodiments discussed below to detection of the health (and particularly the damage) that occurs in each of an optical fiber core of medical instrument including (i) a single core fiber, and (ii) a plurality of core fibers. It is noted that in addition to strain altering the shape of a sensor, ambient temperature variations may also alter the shape of a sensor, thereby causing variations (shifts) in the wavelength of the reflected light from the sensors positioned on the optical fiber core.

Specific embodiments of the disclosure include utilization of a medical instrument, such as a stylet, featuring a multi-core optical fiber and a conductive medium that collectively operate for tracking placement with a body of a patient of the stylet or another medical instrument (such as a catheter) in which the stylet is disposed. In lieu of a stylet, a guidewire may be utilized. For convenience, embodiments are generally discussed where the optical fiber core is disposed within a stylet; however, the disclosure is not intended to be so limited as the functionality involving detection of the health of an optical fiber core disclosed herein may be implemented regardless of the medical instrument in which the optical fiber core is disposed. In some embodiments, the optical fiber core may be integrated directly into a wall of the catheter.

In some embodiments, the optical fiber core of a stylet is configured to return information for use in identifying its physical state (e.g., shape length, shape, and/or form) of (i) a portion of the stylet (e.g., tip, segment of stylet, etc.) or a portion of a catheter inclusive of at least a portion of the stylet (e.g., tip, segment of catheter, etc.) or (ii) the entirety or a substantial portion of the stylet or catheter within the body of a patient (hereinafter, described as the "physical state of the stylet" or the "physical state of the catheter"). According to one embodiment of the disclosure, the returned information may be obtained from reflected light signals of different spectral widths, where each reflected light signal corresponds to a portion of broadband incident light propagating along a core of the multi-core optical fiber (core fiber) that is reflected back over the core fiber by a particular sensor located on the core fiber. One illustrative example of the returned information may pertain to a change in signal characteristics of the reflected light signal returned from the sensor, where wavelength shift is correlated to (mechanical) strain on the core fiber or a detected change in ambient temperature.

In some embodiments, the core fiber utilizes a plurality of sensors and each sensor is configured to reflect a different spectral range of the incident light (e.g., different light frequency range). Based on the type and degree of strain asserted on each core fiber, the sensors associated with that core fiber may alter (shift) the wavelength of the reflected light to convey the type and degree of stain on that core fiber at those locations of the stylet occupied by the sensors. The sensors are spatially distributed at various locations of the core fiber between a proximal end and a distal end of the stylet so that shape sensing of the stylet may be conducted based on analytics of the wavelength shifts. Herein, the shape sensing functionality is paired with the ability to simultaneously pass an electrical signal through the same member (stylet) through conductive medium included as part of the stylet.

Similarly, the sensors may alter (shift) the wavelength of the reflected light to convey sensed variations in ambient temperature. The alterations in response to detected variations in ambient temperature thereby provide for a temperature sensing functionality.

More specifically, in some embodiments each core fiber of the multi-core optical fiber is configured with an array of sensors, which are spatially distributed over a prescribed length of the core fiber to generally sense external strain on or variations in ambient temperature proximate those regions of the core fiber occupied by the sensor. Given that each sensor positioned along the same core fiber is configured to reflect light of a different, specific spectral width, the array of sensors enables distributed measurements throughout the prescribed length of the multi-core optical fiber. These distributed measurements may include wavelength shifts having a correlation with strain experienced and/or temperature variations detected by the sensor.

In more detail, each sensor may operate as a reflective grating such as a fiber Bragg grating (FBG), namely an intrinsic sensor corresponding to a permanent, periodic refractive index change inscribed into the core fiber. Stated differently, the sensor operates as a light reflective mirror for a specific spectral width (e.g., a specific wavelength or specific range of wavelengths). As a result, as broadband incident light is supplied by an optical light source and propagates through a particular core fiber, upon reaching a first sensor of the distributed array of sensors for that core fiber, light of a prescribed spectral width associated with the first sensor is reflected back to an optical receiver within a console, including a display and the optical light source. The remaining spectrum of the incident light continues propagation through the core fiber toward a distal end of the stylet. The remaining spectrum of the incident light may encounter other sensors from the distributed array of sensors, where each of these sensors is fabricated to reflect light with different specific spectral widths to provide distributed measurements, as described above.

During operation, multiple light reflections (also referred to as "reflected light signals") are returned to the console from each of the plurality of core fibers of the multi-core optical fiber. Each reflected light signal may be uniquely associated with a different spectral width. Information associated with the reflected light signals may be used to determine a three-dimensional representation of the physical state of the stylet within the body of a patient through detection of strain in response to emitted incident light. Herein, the core fibers are spatially separated with the cladding of the multi-mode optical fiber and each core fiber is configured to separately return light of different spectral widths (e.g., specific light wavelength or a range of light wavelengths) reflected from the distributed array of sensors fabricated in each of the core fibers.

During vasculature insertion and advancement of the catheter, the clinician may rely on the console to visualize a current physical state (e.g., shape) of a catheter guided by the stylet to avoid potential path deviations. As the periphery core fibers reside at spatially different locations within the cladding of the multi-mode optical fiber, changes in angular orientation (such as bending with respect to the center core fiber, etc.) of the stylet imposes different types (e.g., compression or tension) and degrees of strain on each of the periphery core fibers as well as the center core fiber. The different types and/or degree of strain may cause the sensors of the core fibers to apply different wavelength shifts, which can be measured to extrapolate the physical state of the stylet (catheter).

Additionally, in some embodiments, a predetermined bend may be created within the optical fiber transmitting incident light and reflected light signals between a console and the optically-enabled medical instrument such that the predetermined bend results in a constant and consistent wavelength shift such that logic of the console may determine a positioning and orientation of the medical instrument, and particularly a distal tip thereof, relative to the known bend. Determining the positioning and orientation of the medical instrument enables the logic to generate an image of the medical instrument in space relative to the known bend, the image may then be utilized as an overlay on an ultrasound image providing a clinician a visual representation of the positioning and orientation of the medical instrument within the ultrasound imaging area. In some embodiments, the predetermined bend may be due to attaching the optical fiber to an ultrasound probe such that the positioning and orientation of the medical instrument are determined relative to the positioning of the ultrasound probe.

Embodiments of the disclosure may include a combination of one or more of the methodologies to confirm that an optical fiber within a medical instrument (e.g., an introducer wire, a guidewire, a stylet within a needle, a needle with fiber optic inlayed into the cannula, a stylet configured for use with a catheter, an optical fiber between a needle and a catheter, and/or an optical fiber integrated into a catheter) is located at a specified location with the vasculature based on oximetry readings determined from light reflected from one or more sensors disposed at the distal tip of the optical fiber.

Herein, some embodiments disclose a medical instrument system for inserting a medical instrument within a patient body, the system comprising the medical instrument comprising a first optical fiber having one or more of core fibers, an interconnect, wherein a distal end of the interconnect is optically coupled to the medical instrument, the interconnect including a second optical fiber having one or more of core fibers, wherein a predetermined bend is formed in the interconnect at a point along the length of the interconnect, and a console optically coupled to a proximal end of the interconnect. The console includes one or more processors and a non-transitory computer-readable medium having stored thereon logic, when executed by the one or more processors, causes operations including providing an incident light signal to the first optical fiber and the second optical fiber, receiving reflected light signals of different spectral widths of the incident light from the first optical fiber and the second optical fiber, processing the reflected light signals to determine a positioning and an orientation of the medical instrument relative to the predetermined bend, generating a display of the medical instrument based on the reflected light signals and the determination of the positioning and the orientation of the medical instrument relative to the predetermined bend, and causing rendering of the display of the medical instrument on a display screen.

In some embodiments, the medical instrument includes a stylet. In additional embodiments, the medical instrument further includes a needle, and wherein the stylet is disposed within a lumen of the needle. In some embodiments, the system further comprises an ultrasound probe coupled to the console, wherein the interconnect is coupled to the ultrasound probe causing the predetermined bend in the interconnect such that the positioning and the orientation of the medical instrument is determined relative to the ultrasound probe. In some embodiments, the logic, when executed by the one or more processors, causes further operations including receiving ultrasound imaging data from the ultrasound probe, and causing rendering of an ultrasound image from the ultrasound imaging data, wherein the display of the medical instrument is rendered as an overlay on the ultrasound image.

In yet further embodiments, the interconnect is coupled to the patient causing the predetermined bend in the interconnect such that the positioning and the orientation of the medical instrument is determined relative to the patient. In some embodiments, each of the one or more core fibers of the first optical fiber and the second optical fiber includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of a corresponding optical fiber.

In yet additional embodiments, the optical fiber is a single-core optical fiber, and wherein the incident light is provided in pulses. In some embodiments, the optical fiber is a multi-core optical fiber including a plurality of core fibers. In some embodiments, the medical instrument is one of an introducer wire, a guidewire, a needle with the first optical fiber inlayed into a cannula of the needle or a catheter with the first optical fiber inlayed into one or more walls of the catheter.

Other embodiments disclose a method for inserting a medical instrument within a patient body, the method comprising providing an incident light signal to a first optical fiber included within the medical instrument and a second optical fiber included within an interconnect, wherein each of the first optical fiber and the second optical fiber include one or more of core fibers, and wherein a distal end of the interconnect is optically coupled to the medical instrument, receiving reflected light signals of different spectral widths of the incident light from the first optical fiber and the second optical fiber, processing the reflected light signals to determine a positioning and an orientation of the medical instrument relative to the predetermined bend, generating a display of the medical instrument based on the reflected light signals and the determination of the positioning and the orientation of the medical instrument relative to the predetermined bend, and causing rendering of the display of the medical instrument on a display screen.

In some embodiments, the medical instrument includes a stylet. In additional embodiments, the medical instrument further includes a needle, and wherein the stylet is disposed within a lumen of the needle. In some embodiments, the system further comprises an ultrasound probe coupled to the console, wherein the interconnect is coupled to the ultrasound probe causing the predetermined bend in the interconnect such that the positioning and the orientation of the medical instrument is determined relative to the ultrasound probe. In some embodiments, the logic, when executed by the one or more processors, causes further operations including receiving ultrasound imaging data from the ultrasound probe, and causing rendering of an ultrasound image from the ultrasound imaging data, wherein the display of the medical instrument is rendered as an overlay on the ultrasound image.

In yet further embodiments, the interconnect is coupled to the patient causing the predetermined bend in the interconnect such that the positioning and the orientation of the medical instrument is determined relative to the patient. In some embodiments, each of the one or more core fibers of the first optical fiber and the second optical fiber includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of a corresponding optical fiber.

In yet additional embodiments, the optical fiber is a single-core optical fiber, and wherein the incident light is provided in pulses. In some embodiments, the optical fiber is a multi-core optical fiber including a plurality of core fibers. In some embodiments, the medical instrument is one of an introducer wire, a guidewire, a needle with the first optical fiber inlayed into a cannula of the needle or a catheter with the first optical fiber inlayed into one or more walls of the catheter.

Still other embodiments disclose a non-transitory, computer-readable medium having logic stored thereon that, when executed by one or more processors, causes operations comprising providing an incident light signal to a first optical fiber included within a medical instrument and a second optical fiber included within an interconnect, wherein each of the first optical fiber and the second optical fiber include one or more of core fibers, and wherein a distal end of the interconnect is optically coupled to the medical instrument, receiving reflected light signals of different spectral widths of the incident light from the first optical fiber and the second optical fiber, processing the reflected light signals to determine a positioning and an orientation of the medical instrument relative to the predetermined bend, generating a display of the medical instrument based on the reflected light signals and the determination of the positioning and the orientation of the medical instrument relative to the predetermined bend, and causing rendering of the display of the medical instrument on a display screen.

In some embodiments, the medical instrument includes a stylet. In additional embodiments, the medical instrument further includes a needle, and wherein the stylet is disposed within a lumen of the needle. In some embodiments, the system further comprises an ultrasound probe coupled to the console, wherein the interconnect is coupled to the ultrasound probe causing the predetermined bend in the interconnect such that the positioning and the orientation of the medical instrument is determined relative to the ultrasound probe. In some embodiments, the logic, when executed by the one or more processors, causes further operations including receiving ultrasound imaging data from the ultrasound probe, and causing rendering of an ultrasound image from the ultrasound imaging data, wherein the display of the medical instrument is rendered as an overlay on the ultrasound image.

In yet further embodiments, the interconnect is coupled to the patient causing the predetermined bend in the interconnect such that the positioning and the orientation of the medical instrument is determined relative to the patient. In some embodiments, each of the one or more core fibers of the first optical fiber and the second optical fiber includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of a corresponding optical fiber.

In yet additional embodiments, the optical fiber is a single-core optical fiber, and wherein the incident light is provided in pulses. In some embodiments, the optical fiber is a multi-core optical fiber including a plurality of core fibers. In some embodiments, the medical instrument is one of an introducer wire, a guidewire, a needle with the first optical fiber inlayed into a cannula of the needle or a catheter with the first optical fiber inlayed into one or more walls of the catheter.

Some embodiments of the disclosure include a medical instrument system for inserting a medical instrument within a patient body, the system comprising the medical instrument comprising a first optical fiber having one or more of core fibers, a console optically coupled to the medical instrument, the console including one or more processors and a non-transitory computer-readable medium having stored thereon logic, when executed by the one or more processors, causes operations including providing an incident light signal to the first optical fiber, receiving reflected light signals of different spectral widths of the incident light from the first optical fiber, processing the reflected light signals to determine a positioning and an orientation of the medical instrument, generating a display of the medical instrument based on the reflected light signals and the determination of the positioning and the orientation of the medical instrument, and causing rendering of the display of the medical instrument on a display screen.

In some embodiments, the system further comprises an interconnect, wherein a distal end of the interconnect is optically coupled to the medical instrument and a proximal end of the interconnect is optically coupled to the console, wherein the interconnect includes a second optical fiber having one or more of core fibers. In some embodiments, the incident light signal and the reflected light signals are transmitted between the console and the medical instrument via the interconnect. In some embodiments, wherein a portion of the interconnect includes a predetermined bend.

In other embodiments, the system further comprises an ultrasound probe coupled to the console via an ultrasound connection, wherein a portion of the interconnect that includes a predetermined bend is coupled to the ultrasound probe. In some embodiments, a length of the interconnect is collocated with the ultrasound connection. In yet other embodiments, the determination of the positioning and the orientation of the medical instrument is relative to the predetermined bend.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which:

FIG. 3A is a first exemplary embodiment of the stylet of FIG. 1A supporting both an optical and electrical signaling in accordance with some embodiments;

FIG. 3B is a cross sectional view of the stylet of FIG. 3A in accordance with some embodiments;

FIG. 4A is a second exemplary embodiment of the stylet of FIG. 1B in accordance with some embodiments;

FIG. 4B is a cross sectional view of the stylet of FIG. 4A in accordance with some embodiments;

DETAILED DESCRIPTION

Figure 1A:
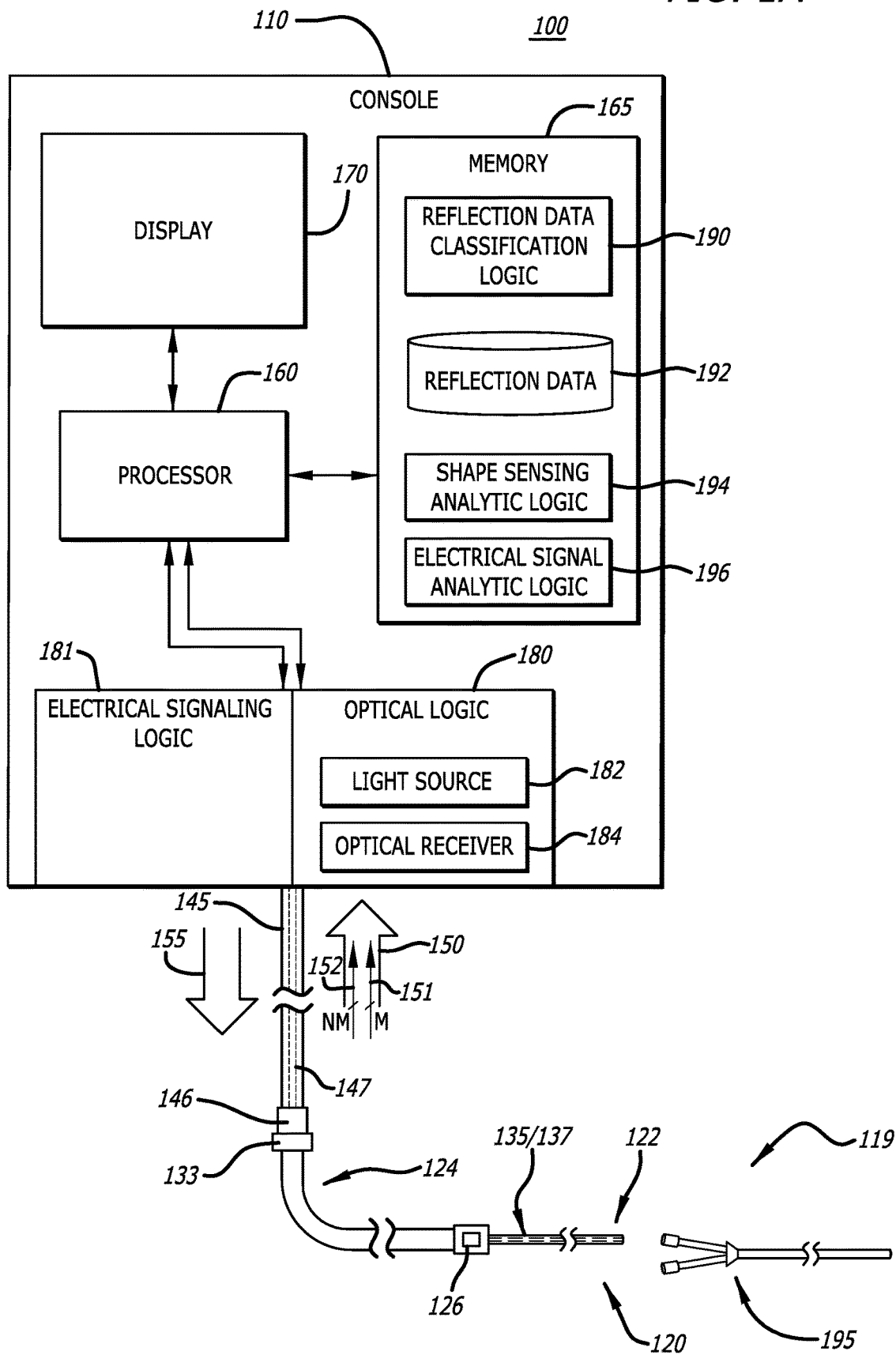
FIG. 1A is an illustrative embodiment of a medical instrument monitoring system including a medical instrument with optic shape sensing and fiber optic-based oximetry capabilities in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a probe disclosed herein includes a portion of the probe intended to be near a clinician when the probe is used on a patient. Likewise, a "proximal length" of, for example, the probe includes a length of the probe intended to be near the clinician when the probe is used on the patient. A "proximal end" of, for example, the probe includes an end of the probe intended to be near the clinician when the probe is used on the patient. The proximal portion, the proximal end portion, or the proximal length of the probe can include the proximal end of the probe; however, the proximal portion, the proximal end portion, or the proximal length of the probe need not include the proximal end of the probe. That is, unless context suggests otherwise, the proximal portion, the proximal end portion, or the proximal length of the probe is not a terminal portion or terminal length of the probe.

With respect to "distal," a "distal portion" or a "distal end portion" of, for example, a probe disclosed herein includes a portion of the probe intended to be near or in a patient when the probe is used on the patient. Likewise, a "distal length" of, for example, the probe includes a length of the probe intended to be near or in the patient when the probe is used on the patient. A "distal end" of, for example, the probe includes an end of the probe intended to be near or in the patient when the probe is used on the patient. The distal portion, the distal end portion, or the distal length of the probe can include the distal end of the probe; however, the distal portion, the distal end portion, or the distal length of the probe need not include the distal end of the probe. That is, unless context suggests otherwise, the distal portion, the distal end portion, or the distal length of the probe is not a terminal portion or terminal length of the probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Referring to FIG. 1A, an illustrative embodiment of a medical instrument monitoring system including a medical instrument with optic shape sensing and fiber optic-based oximetry capabilities is shown in accordance with some embodiments. As shown, the system 100 generally includes a console 110 and a stylet assembly 119 communicatively coupled to the console 110. For this embodiment, the stylet assembly 119 includes an elongate probe (e.g., stylet) 120 on its distal end 122 and a console connector 133 on its proximal end 124. The console connector 133 enables the stylet assembly 119 to be operably connected to the console 110 via an interconnect 145 including one or more optical fibers 147 (hereinafter, "optical fiber(s)") and a conductive medium terminated by a single optical/electric connector 146 (or terminated by dual connectors. Herein, the connector 146 is configured to engage (mate) with the console connector 133 to allow for the propagation of light between the console 110 and the stylet assembly 119 as well as the propagation of electrical signals from the stylet 120 to the console 110.

An exemplary implementation of the console 110 includes a processor 160, a memory 165, a display 170 and optical logic 180, although it is appreciated that the console 110 can take one of a variety of forms and may include additional components (e.g., power supplies, ports, interfaces, etc.) that are not directed to aspects of the disclosure. An illustrative example of the console 110 is illustrated in U.S. Publication No. 2019/0237902, the entire contents of which are incorporated by reference herein. The processor 160, with access to the memory 165 (e.g., non-volatile memory or non-transitory, computer-readable medium), is included to control functionality of the console 110 during operation. As shown, the display 170 may be a liquid crystal diode (LCD) display integrated into the console 110 and employed as a user interface to display information to the clinician, especially during a catheter placement procedure (e.g., cardiac catheterization). In another embodiment, the display 170 may be separate from the console 110. Although not shown, a user interface is configured to provide user control of the console 110.

For both of these embodiments, the content depicted by the display 170 may change according to which mode the stylet 120 is configured to operate: optical, TLS, ECG, or another modality. In TLS mode, the content rendered by the display 170 may constitute a two-dimensional (2D) or three-dimensional (3D) representation of the physical state (e.g., length, shape, form, and/or orientation) of the stylet 120 computed from characteristics of reflected light signals 150 returned to the console 110. The reflected light signals 150 constitute light of a specific spectral width of broadband incident light 155 reflected back to the console 110. According to one embodiment of the disclosure, the reflected light signals 150 may pertain to various discrete portions (e.g., specific spectral widths) of broadband incident light 155 transmitted from and sourced by the optical logic 180, as described below According to one embodiment of the disclosure, an activation control 126, included on the stylet assembly 119, may be used to set the stylet 120 into a desired operating mode and selectively alter operability of the display 170 by the clinician to assist in medical device placement. For example, based on the modality of the stylet 120, the display 170 of the console 110 can be employed for optical modality-based guidance during catheter advancement through the vasculature or TLS modality to determine the physical state (e.g., length, form, shape, orientation, etc.) of the stylet 120. In one embodiment, information from multiple modes, such as optical, TLS or ECG for example, may be displayed concurrently (e.g., at least partially overlapping in time).

Referring still to FIG. 1A, the optical logic 180 is configured to support operability of the stylet assembly 119 and enable the return of information to the console 110, which may be used to determine the physical state associated with the stylet 120 along with monitored electrical signals such as ECG signaling via an electrical signaling logic 181 that supports receipt and processing of the received electrical signals from the stylet 120 (e.g., ports, analog-to-digital conversion logic, etc.). The physical state of the stylet 120 may be based on changes in characteristics of the reflected light signals 150 received at the console 110 from the stylet 120. The characteristics may include shifts in wavelength caused by strain on certain regions of the core fibers integrated within an optical fiber core 135 positioned within or operating as the stylet 120, as shown below. As discussed herein, the optical fiber core 135 may be comprised of core fibers $137_1$-$137_M$ (M=1 for a single core, and M≥2 for a multi-core), where the core fibers $137_1$-$137_M$ may collectively be referred to as core fiber(s) 137. Unless otherwise specified or the instant embodiment requires an alternative interpretation, embodiments discussed herein will refer to a multi-core optical fiber 135. From information associated with the reflected light signals 150, the console 110 may determine (through computation or extrapolation of the wavelength shifts) the physical state of the stylet 120, and also that of a catheter 195 configured to receive the stylet 120.

According to one embodiment of the disclosure, as shown in FIG. 1A, the optical logic 180 may include a light source 182 and an optical receiver 184. The light source 182 is configured to transmit the incident light 155 (e.g., broadband) for propagation over the optical fiber(s) 147 included in the interconnect 145, which are optically connected to the multi-core optical fiber core 135 within the stylet 120. In one embodiment, the light source 182 is a tunable swept laser, although other suitable light sources can also be employed in addition to a laser, including semi-coherent light sources, LED light sources, etc.

The optical receiver 184 is configured to: (i) receive returned optical signals, namely reflected light signals 150 received from optical fiber-based reflective gratings (sensors) fabricated within each core fiber of the multi-core optical fiber 135 deployed within the stylet 120, and (ii) translate the reflected light signals 150 into reflection data 192, namely data in the form of electrical signals representative of the reflected light signals including wavelength shifts caused by strain. The reflected light signals 150 associated with different spectral widths may include reflected light signals 151 provided from sensors positioned in the center core fiber (reference) of the multi-core optical fiber 135 and reflected light signals 152 provided from sensors positioned in the periphery core fibers of the multi-core optical fiber 135, as described below. Herein, the optical receiver 184 may be implemented as a photodetector, such as a positive-intrinsic-negative "PIN" photodiode, avalanche photodiode, or the like.

As shown, both the light source 182 and the optical receiver 184 are operably connected to the processor 160, which governs their operation. Also, the optical receiver 184 is operably coupled to provide the reflection data 192 to the memory 165 for storage and processing by reflection data classification logic 190. The reflection data classification logic 190 may be configured to: (i) identify which core fibers pertain to which of the received reflection data 192 and (ii) segregate the reflection data 192 provided from reflected light signals 150 pertaining to similar regions of the stylet 120 or spectral widths into analysis groups. The reflection data for each analysis group is made available to shape sensing analytic logic 194 for analytics.

According to one embodiment of the disclosure, the shape sensing analytic logic 194 is configured to compare wavelength shifts measured by sensors deployed in each periphery core fiber at the same measurement region of the stylet 120 (or same spectral width) to the wavelength shift at a center core fiber of the multi-core optical fiber 135 positioned along central axis and operating as a neutral axis of bending. From these analytics, the shape sensing analytic logic 194 may determine the shape the core fibers have taken in 3D space and may further determine the current physical state of the catheter 195 in 3D space for rendering on the display 170.

According to one embodiment of the disclosure, the shape sensing analytic logic 194 may generate a rendering of the current physical state of the stylet 120 (and potentially the catheter 195), based on heuristics or run-time analytics. For example, the shape sensing analytic logic 194 may be configured in accordance with machine-learning techniques to access a data store (library) with pre-stored data (e.g., images, etc.) pertaining to different regions of the stylet 120 (or catheter 195) in which reflected light from core fibers have previously experienced similar or identical wavelength shifts. From the pre-stored data, the current physical state of the stylet 120 (or catheter 195) may be rendered. Alternatively, as another example, the shape sensing analytic logic 194 may be configured to determine, during run-time, changes in the physical state of each region of the multi-core optical fiber 135 based on at least: (i) resultant wavelength shifts experienced by different core fibers within the optical fiber 135, and (ii) the relationship of these wavelength shifts generated by sensors positioned along different periphery core fibers at the same cross-sectional region of the multi-core optical fiber 135 to the wavelength shift generated by a sensor of the center core fiber at the same cross-sectional region. It is contemplated that other processes and procedures may be performed to utilize the wavelength shifts as measured by sensors along each of the core fibers within the multi-core optical fiber 135 to render appropriate changes in the physical state of the stylet 120 (and/or catheter 195), especially to enable guidance of the stylet 120, when positioned at a distal tip of the catheter 195, within the vasculature of the patient and at a desired destination within the body.

The console 110 may further include electrical signaling logic 181, which is positioned to receive one or more electrical signals from the stylet 120. The stylet 120 is configured to support both optical connectivity as well as electrical connectivity. The electrical signaling logic 181 receives the electrical signals (e.g., ECG signals) from the stylet 120 via the conductive medium. The electrical signals may be processed by electrical signal analytic logic 196, executed by the processor 160, to determine ECG waveforms for display.

Figure 1B:
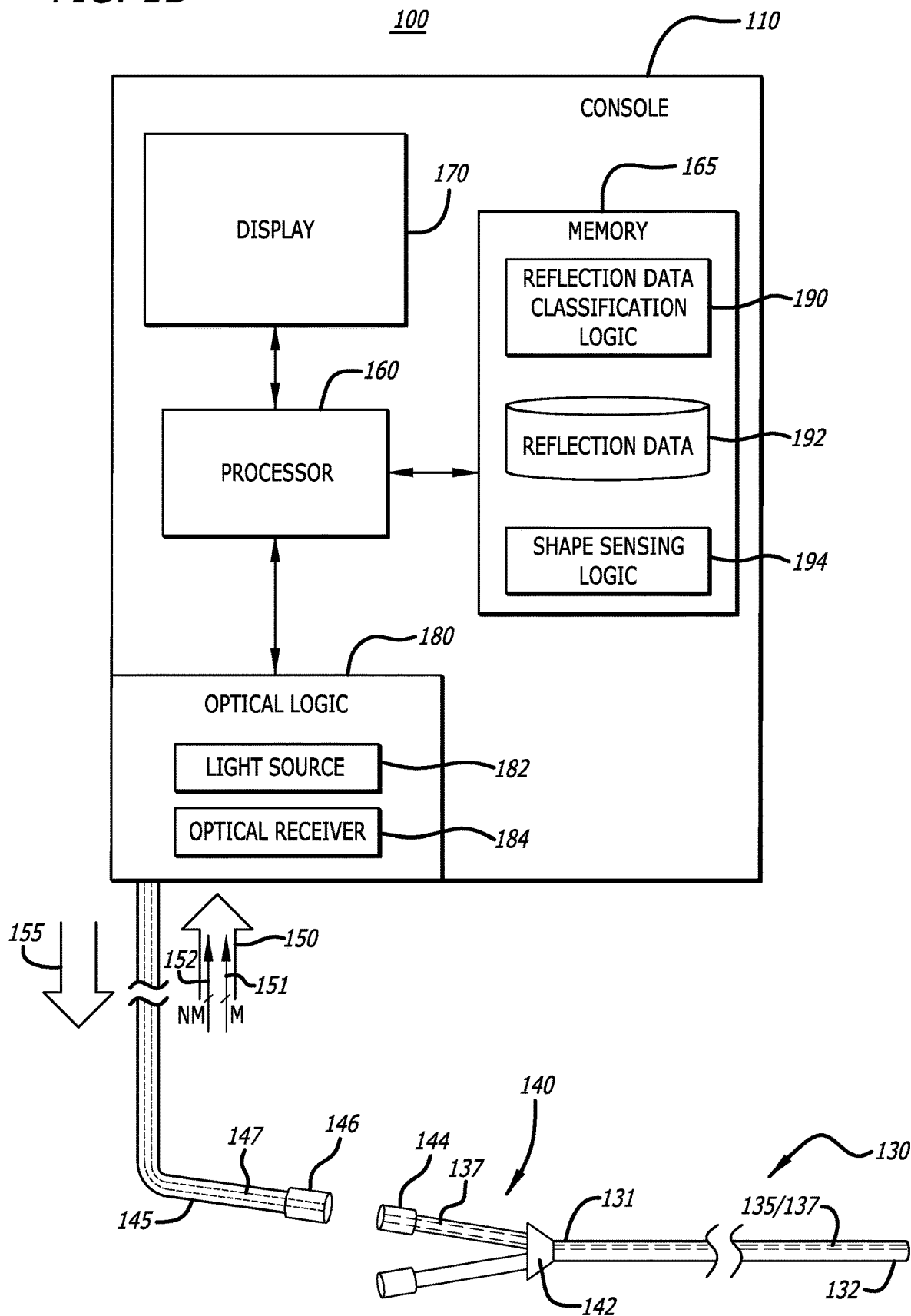
FIG. 1B is an alternative illustrative embodiment of the medical instrument monitoring system 100 in accordance with some embodiments.

Referring to FIG. 1B, an alternative exemplary embodiment of a medical instrument monitoring system 100 is shown. Herein, the medical instrument monitoring system 100 features a console 110 and a medical instrument 130 communicatively coupled to the console 110. For this embodiment, the medical instrument 130 corresponds to a catheter, which features an integrated tubing with two or more lumen extending between a proximal end 131 and a distal end 132 of the integrated tubing. The integrated tubing (sometimes referred to as "catheter tubing") is in communication with one or more extension legs 140 via a bifurcation hub 142. An optical-based catheter connector 144 may be included on a proximal end of at least one of the extension legs 140 to enable the catheter 130 to operably connect to the console 110 via an interconnect 145 or another suitable component. Herein, the interconnect 145 may include a connector 146 that, when coupled to the optical-based catheter connector 144, establishes optical connectivity between one or more optical fibers 147 (hereinafter, "optical fiber(s)") included as part of the interconnect 145 and core fibers 137 deployed within the catheter 130 and integrated into the tubing. Alternatively, a different combination of connectors, including one or more adapters, may be used to optically connect the optical fiber(s) 147 to the core fibers 137 within the catheter 130. The core fibers 137 deployed within the catheter 130 as illustrated in FIG. 1B include the same characteristics and perform the same functionalities as the core fibers 137 deployed within the stylet 120 of FIG. 1A.

The optical logic 180 is configured to support graphical rendering of the catheter 130, most notably the integrated tubing of the catheter 130, based on characteristics of the reflected light signals 150 received from the catheter 130. The characteristics may include shifts in wavelength caused by strain on certain regions of the core fibers 137 integrated within (or along) a wall of the integrated tubing, which may be used to determine (through computation or extrapolation of the wavelength shifts) the physical state of the catheter 130, notably its integrated tubing or a portion of the integrated tubing such as a tip or distal end of the tubing to read fluctuations (real-time movement) of the tip (or distal end).

More specifically, the optical logic 180 includes a light source 182. The light source 182 is configured to transmit the broadband incident light 155 for propagation over the optical fiber(s) 147 included in the interconnect 145, which are optically connected to multiple core fibers 137 within the catheter tubing. Herein, the optical receiver 184 is configured to: (i) receive returned optical signals, namely reflected light signals 150 received from optical fiber-based reflective gratings (sensors) fabricated within each of the core fibers 137 deployed within the catheter 130, and (ii) translate the reflected light signals 150 into reflection data 192, namely data in the form of electrical signals representative of the reflected light signals including wavelength shifts caused by strain. The reflected light signals 150 associated with different spectral widths include reflected light signals 151 provided from sensors positioned in the center core fiber (reference) of the catheter 130 and reflected light signals 152 provided from sensors positioned in the outer core fibers of the catheter 130, as described below.

As noted above, the shape sensing logic 194 is configured to compare wavelength shifts measured by sensors deployed in each outer core fiber at the same measurement region of the catheter (or same spectral width) to the wavelength shift at the center core fiber positioned along central axis and operating as a neutral axis of bending. From these analytics, the shape sensing logic 190 may determine the shape the core fibers have taken in 3D space and may further determine the current physical state of the catheter 130 in 3D space for rendering on the display 170.

According to one embodiment of the disclosure, the shape sensing logic 194 may generate a rendering of the current physical state of the catheter 130, especially the integrated tubing, based on heuristics or run-time analytics. For example, the shape sensing logic 194 may be configured in accordance with machine-learning techniques to access a data store (library) with pre-stored data (e.g., images, etc.) pertaining to different regions of the catheter 130 in which the core fibers 137 experienced similar or identical wavelength shifts. From the pre-stored data, the current physical state of the catheter 130 may be rendered. Alternatively, as another example, the shape sensing logic 194 may be configured to determine, during run-time, changes in the physical state of each region of the catheter 130, notably the tubing, based on at least (i) resultant wavelength shifts experienced by the core fibers 137 and (ii) the relationship of these wavelength shifts generated by sensors positioned along different outer core fibers at the same cross-sectional region of the catheter 130 to the wavelength shift generated by a sensor of the center core fiber at the same cross-sectional region. It is contemplated that other processes and procedures may be performed to utilize the wavelength shifts as measured by sensors along each of the core fibers 137 to render appropriate changes in the physical state of the catheter 130.

Figure 2:
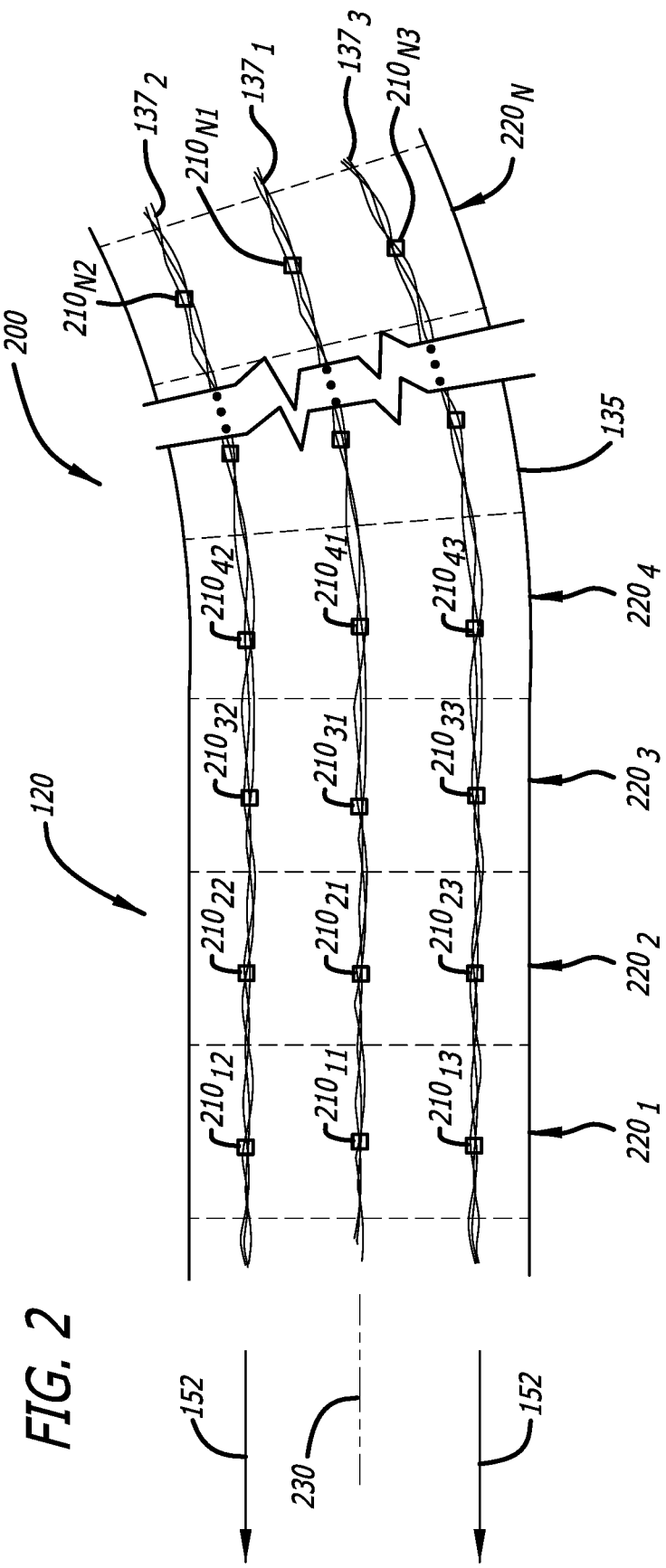
FIG. 2 is an exemplary embodiment of a structure of a section of the multi-core optical fiber included within the stylet 120 of FIG. 1A in accordance with some embodiments.

Referring to FIG. 2, an exemplary embodiment of a structure of a section of the multi-core optical fiber included within the stylet 120 of FIG. 1A is shown in accordance with some embodiments. The multi-core optical fiber section 200 of the multi-core optical fiber 135 depicts certain core fibers $137_1$-$137_M$ (M≥2, M=4 as shown, see FIG. 3A) along with the spatial relationship between sensors (e.g., reflective gratings) $210_{11}$-$210_{NM}$ (N≥2; M≥2) present within the core fibers $137_1$-$137_M$, respectively. As noted above, the core fibers $137_1$-$137_M$ may be collectively referred to as "the core fibers 137."

As shown, the section 200 is subdivided into a plurality of cross-sectional regions $220_1$-$220_N$, where each cross-sectional region $220_1$-$220_N$ corresponds to reflective gratings $210_{11}$-$210_{14}$ . . . $210_{N1}$-$210_{N4}$. Some or all of the cross-sectional regions $220_1$ . . . $220_N$ may be static (e.g., prescribed length) or may be dynamic (e.g., vary in size among the regions $220_1$ . . . $220_N$). A first core fiber $137_1$ is positioned substantially along a center (neutral) axis 230 while core fiber $137_2$ may be oriented within the cladding of the multi-core optical fiber 135, from a cross-sectional, front-facing perspective, to be position on "top" the first core fiber $137_1$. In this deployment, the core fibers $137_3$ and $137_4$ may be positioned "bottom left" and "bottom right" of the first core fiber $137_1$. As examples, FIGS. 3A-4B provides illustrations of such.

Referencing the first core fiber $137_1$ as an illustrative example, when the stylet 120 is operative, each of the reflective gratings $210_1$-$210_N$ reflects light for a different spectral width. As shown, each of the gratings $210_{1i}$-$210_{Ni}$ (1≤i≤M) is associated with a different, specific spectral width, which would be represented by different center frequencies of $f_1$ . . . $f_N$, where neighboring spectral widths reflected by neighboring gratings are non-overlapping according to one embodiment of the disclosure.

Herein, positioned in different core fibers $137_2$-$137_3$ but along at the same cross-sectional regions 220-$220_N$ of the multi-core optical fiber 135, the gratings $210_{12}$-$210_{N2}$ and $210_{13}$-$210_{N3}$ are configured to reflect incoming light at same (or substantially similar) center frequency. As a result, the reflected light returns information that allows for a determination of the physical state of the optical fibers 137 (and the stylet 120) based on wavelength shifts measured from the returned, reflected light. In particular, strain (e.g., compression or tension) applied to the multi-core optical fiber 135 (e.g., at least core fibers $137_2$-$137_3$) results in wavelength shifts associated with the returned, reflected light. Based on different locations, the core fibers $137_1$-$137_4$ experience different types and degree of strain based on angular path changes as the stylet 120 advances in the patient.

For example, with respect to the multi-core optical fiber section 200 of FIG. 2, in response to angular (e.g., radial) movement of the stylet 120 is in the left-veering direction, the fourth core fiber $137_4$ (see FIG. 3A) of the multi-core optical fiber 135 with the shortest radius during movement (e.g., core fiber closest to a direction of angular change) would exhibit compression (e.g., forces to shorten length). At the same time, the third core fiber $137_3$ with the longest radius during movement (e.g., core fiber furthest from the direction of angular change) would exhibit tension (e.g., forces to increase length). As these forces are different and unequal, the reflected light from reflective gratings $210_{N2}$ and $210_{N3}$ associated with the core fiber $137_2$ and $137_3$ will exhibit different changes in wavelength. The differences in wavelength shift of the reflected light signals 150 can be used to extrapolate the physical configuration of the stylet 120 by determining the degrees of wavelength change caused by compression/tension for each of the periphery fibers (e.g., the second core fiber $137_2$ and the third core fiber $137_3$) in comparison to the wavelength of the reference core fiber (e.g., first core fiber $137_1$) located along the neutral axis 230 of the multi-core optical fiber 135. These degrees of wavelength change may be used to extrapolate the physical state of the stylet 120. The reflected light signals 150 are reflected back to the console 110 via individual paths over a particular core fiber $137_1$-$137_M$.

Referring to FIG. 3A, a first exemplary embodiment of the stylet of FIG. 1A supporting both an optical and electrical signaling is shown in accordance with some embodiments. Herein, the stylet 120 features a centrally located multi-core optical fiber 135, which includes a cladding 300 and a plurality of core fibers $137_1$-$137_M$ (M≥2; M=4) residing within a corresponding plurality of lumens $320_1$-$320_M$. While the multi-core optical fiber 135 is illustrated within four (4) core fibers $137_1$-$137_4$, a greater number of core fibers $137_1$-$137_M$ (M>4) may be deployed to provide a more detailed three-dimensional sensing of the physical state (e.g., shape, etc.) of the multi-core optical fiber 135 and the stylet 120 deploying the optical fiber 135.

For this embodiment of the disclosure, the multi-core optical fiber 135 is encapsulated within a concentric braided tubing 310 positioned over a low coefficient of friction layer 335. The braided tubing 310 may feature a "mesh" construction, in which the spacing between the intersecting conductive elements is selected based on the degree of rigidity desired for the stylet 120, as a greater spacing may provide a lesser rigidity, and thereby, a more pliable stylet 120.

According to this embodiment of the disclosure, as shown in FIGS. 3A-3B, the core fibers $137_1$-$137_4$ include (i) a central core fiber $137_1$ and (ii) a plurality of periphery core fibers $137_2$-$137_4$, which are maintained within lumens $320_1$-$320_4$ formed in the cladding 300. According to one embodiment of the disclosure, one or more of the lumen $320_1$-$320_4$ may be configured with a diameter sized to be greater than the diameter of the core fibers $137_1$-$137_4$. By avoiding a majority of the surface area of the core fibers $137_1$-$137_4$ from being in direct physical contact with a wall surface of the lumens $320_1$-$320_4$, the wavelength changes to the incident light are caused by angular deviations in the multi-core optical fiber 135 thereby reducing influence of compression and tension forces being applied to the walls of the lumens $320_1$-$320_M$, not the core fibers $137_1$-$137_M$ themselves.

As further shown in FIGS. 3A-3B, the core fibers $137_1$-$137_4$ may include central core fiber $137_1$ residing within a first lumen $320_1$ formed along the first neutral axis 230 and a plurality of core fibers $137_2$-$137_4$ residing within lumens $320_2$-$320_4$ each formed within different areas of the cladding 300 radiating from the first neutral axis 230. In general, the core fibers $137_2$-$137_4$, exclusive of the central core fiber $137_1$, may be positioned at different areas within a cross-sectional area 305 of the cladding 300 to provide sufficient separation to enable three-dimensional sensing of the multi-core optical fiber 135 based on changes in wavelength of incident light propagating through the core fibers $137_2$-$137_4$ and reflected back to the console for analysis.

For example, where the cladding 300 features a circular cross-sectional area 305 as shown in FIG. 3B, the core fibers $137_2$-$137_4$ may be positioned substantially equidistant from each other as measured along a perimeter of the cladding 300, such as at "top" (12 o'clock), "bottom-left" (8 o'clock) and "bottom-right" (4 o'clock) locations as shown. Hence, in general terms, the core fibers $137_2$-$137_4$ may be positioned within different segments of the cross-sectional area 305. Where the cross-sectional area 305 of the cladding 300 has a distal tip 330 and features a polygon cross-sectional shape (e.g., triangular, square, rectangular, pentagon, hexagon, octagon, etc.), the central core fiber $137_1$ may be located at or near a center of the polygon shape, while the remaining core fibers $137_2$-$137_M$ may be located proximate to angles between intersecting sides of the polygon shape.

Referring still to FIGS. 3A-3B, operating as the conductive medium for the stylet 120, the braided tubing 310 provides mechanical integrity to the multi-core optical fiber 135 and operates as a conductive pathway for electrical signals. For example, the braided tubing 310 may be exposed to a distal tip of the stylet 120. The cladding 300 and the braided tubing 310, which is positioned concentrically surrounding a circumference of the cladding 300, are contained within the same insulating layer 350. The insulating layer 350 may be a sheath or conduit made of protective, insulating (e.g., non-conductive) material that encapsulates both for the cladding 300 and the braided tubing 310, as shown.

Referring to FIG. 4A, a second exemplary embodiment of the stylet of FIG. 1B is shown in accordance with some embodiments. Referring now to FIG. 4A, a second exemplary embodiment of the stylet 120 of FIG. 1B supporting both an optical and electrical signaling is shown. Herein, the stylet 120 features the multi-core optical fiber 135 described above and shown in FIG. 3A, which includes the cladding 300 and the first plurality of core fibers $137_1$-$137_M$ (M≥3; M=4 for embodiment) residing within the corresponding plurality of lumens $320_1$-$320_M$. For this embodiment of the disclosure, the multi-core optical fiber 135 includes the central core fiber $137_1$ residing within the first lumen $320_1$ formed along the first neutral axis 230 and the second plurality of core fibers $137_2$-$137_4$ residing within corresponding lumens $320_2$-$320_4$ positioned in different segments within the cross-sectional area 305 of the cladding 300. Herein, the multi-core optical fiber 135 is encapsulated within a conductive tubing 400. The conductive tubing 400 may feature a "hollow" conductive cylindrical member concentrically encapsulating the multi-core optical fiber 135.

Referring to FIGS. 4A-4B, operating as a conductive medium for the stylet 120 in the transfer of electrical signals (e.g., ECG signals) to the console, the conductive tubing 400 may be exposed up to a tip 410 of the stylet 120. For this embodiment of the disclosure, a conductive epoxy 420 (e.g., metal-based epoxy such as a silver epoxy) may be affixed to the tip 410 and similarly joined with a termination/connection point created at a proximal end 430 of the stylet 120. The cladding 300 and the conductive tubing 400, which is positioned concentrically surrounding a circumference of the cladding 300, are contained within the same insulating layer 440. The insulating layer 440 may be a protective conduit encapsulating both for the cladding 300 and the conductive tubing 400, as shown.

Figure 5A:
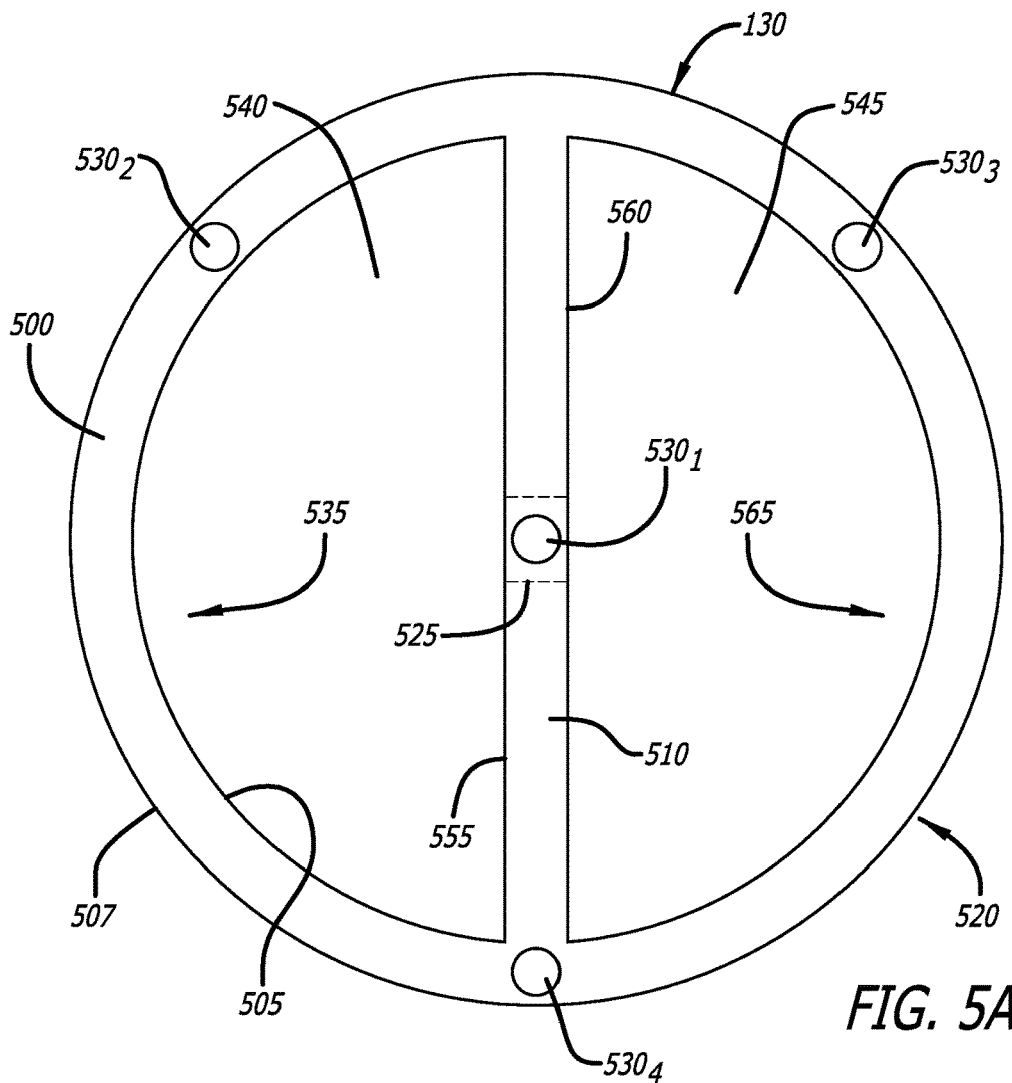
FIG. 5A is an elevation view of a first illustrative embodiment of a catheter including integrated tubing, a diametrically disposed septum, and micro-lumens formed within the tubing and septum in accordance with some embodiments.

Referring to FIG. 5A, an elevation view of a first illustrative embodiment of a catheter including integrated tubing, a diametrically disposed septum, and micro-lumens formed within the tubing and septum is shown in accordance with some embodiments. Herein, the catheter 130 includes integrated tubing, the diametrically disposed septum 510, and the plurality of micro-lumens $530_1$-$530_4$ which, for this embodiment, are fabricated to reside within the wall 500 of the integrated tubing of the catheter 130 and within the septum 510. In particular, the septum 510 separates a single lumen, formed by the inner surface 505 of the wall 500 of the catheter 130, into multiple lumen, namely two lumens 540 and 545 as shown. Herein, the first lumen 540 is formed between a first arc-shaped portion 535 of the inner surface 505 of the wall 500 forming the catheter 130 and a first outer surface 555 of the septum 510 extending longitudinally within the catheter 130. The second lumen 545 is formed between a second arc-shaped portion 565 of the inner surface 505 of the wall 500 forming the catheter 130 and a second outer surfaces 560 of the septum 510.

According to one embodiment of the disclosure, the two lumens 540 and 545 have approximately the same volume. However, the septum 510 need not separate the tubing into two equal lumens. For example, instead of the septum 510 extending vertically (12 o'clock to 6 o'clock) from a front-facing, cross-sectional perspective of the tubing, the septum 510 could extend horizontally (3 o'clock to 9 o'clock), diagonally (1 o'clock to 7 o'clock; 10 o'clock to 4 o'clock) or angularly (2 o'clock to 10 o'clock). In the later configuration, each of the lumens 540 and 545 of the catheter 130 would have a different volume.

With respect to the plurality of micro-lumens $530_1$-$530_4$, the first micro-lumen $530_1$ is fabricated within the septum 510 at or near the cross-sectional center 525 of the integrated tubing. For this embodiment, three micro-lumens $530_2$-$530_4$ are fabricated to reside within the wall 500 of the catheter 130. In particular, a second micro-lumen $530_2$ is fabricated within the wall 500 of the catheter 130, namely between the inner surface 505 and outer surface 507 of the first arc-shaped portion 535 of the wall 500. Similarly, the third micro-lumen $530_3$ is also fabricated within the wall 500 of the catheter 130, namely between the inner and outer surfaces 505/507 of the second arc-shaped portion 555 of the wall 500. The fourth micro-lumen $530_4$ is also fabricated within the inner and outer surfaces 505/507 of the wall 500 that are aligned with the septum 510.

According to one embodiment of the disclosure, as shown in FIG. 5A, the micro-lumens $530_2$-$530_4$ are positioned in accordance with a "top-left" (10 o'clock), "top-right" (2 o'clock) and "bottom" (6 o'clock) layout from a front-facing, cross-sectional perspective. Of course, the micro-lumens $530_2$-$530_4$ may be positioned differently, provided that the micro-lumens $530_2$-$530_4$ are spatially separated along the circumference 520 of the catheter 130 to ensure a more robust collection of reflected light signals from the outer core fibers $570_2$-$570_4$ when installed. For example, two or more of micro-lumens (e.g., micro-lumens $530_2$ and $530_4$) may be positioned at different quadrants along the circumference 520 of the catheter wall 500.

Figure 5B:
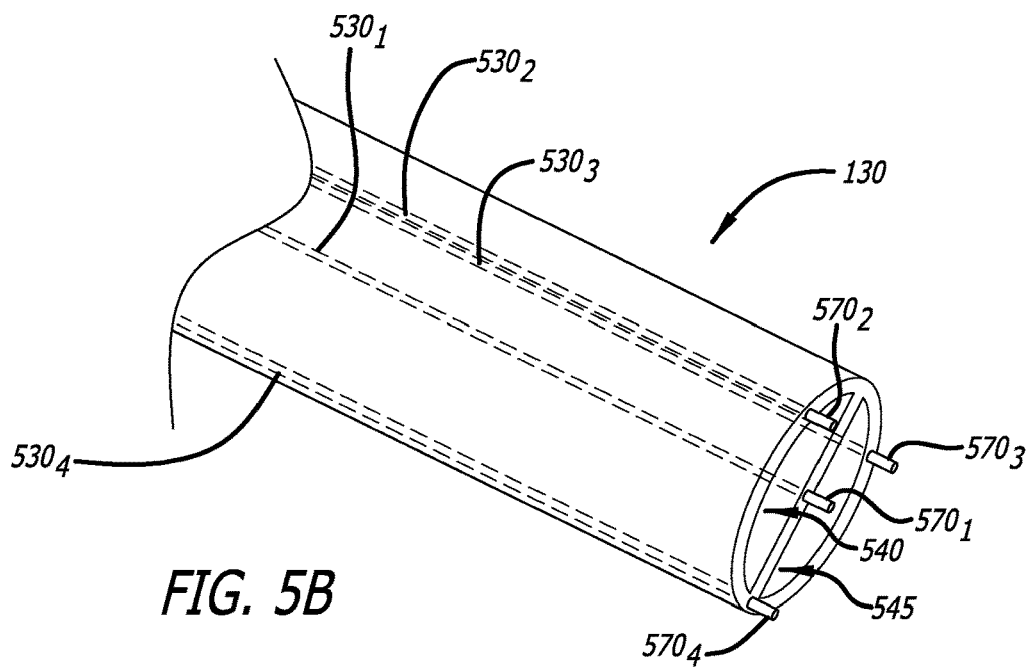
FIG. 5B is a perspective view of the first illustrative embodiment of the catheter of FIG. 5A including core fibers installed within the micro-lumens in accordance with some embodiments.

Referring to FIG. 5B, a perspective view of the first illustrative embodiment of the catheter of FIG. 5A including core fibers installed within the micro-lumens is shown in accordance with some embodiments. According to one embodiment of the disclosure, the second plurality of micro-lumens $530_2$-$530_4$ are sized to retain corresponding outer core fibers $570_2$-$570_4$, where the diameter of each of the second plurality of micro-lumens $530_2$-$530_4$ may be sized just larger than the diameters of the outer core fibers $570_2$-$570_4$. The size differences between a diameter of a single core fiber and a diameter of any of the micro-lumen $530_1$-$530_4$ may range between 0.001 micrometers (μm) and 1000 μm, for example. As a result, the cross-sectional areas of the outer core fibers $570_2$-$570_4$ would be less than the cross-sectional areas of the corresponding micro-lumens $530_2$-$530_4$. A "larger" micro-lumen (e.g., micro-lumen $530_2$)

may better isolate external strain being applied to the outer core fiber $570_2$ from strain directly applied to the catheter 130 itself. Similarly, the first micro-lumen $530_1$ may be sized to retain the center core fiber $570_1$, where the diameter of the first micro-lumen $530_1$ may be sized just larger than the diameter of the center core fiber $570_1$.

As an alternative embodiment of the disclosure, one or more of the micro-lumens $530_1$-$530_4$ may be sized with a diameter that exceeds the diameter of the corresponding one or more core fibers $570_1$-$570_4$. However, at least one of the micro-lumens $530_1$-$530_4$ is sized to fixedly retain their corresponding core fiber (e.g., core fiber retained with no spacing between its lateral surface and the interior wall surface of its corresponding micro-lumen). As yet another alternative embodiment of the disclosure, all the micro-lumens $530_1$-$530_4$ are sized with a diameter to fixedly retain the core fibers $570_1$-$570_4$.

Figure 6A:
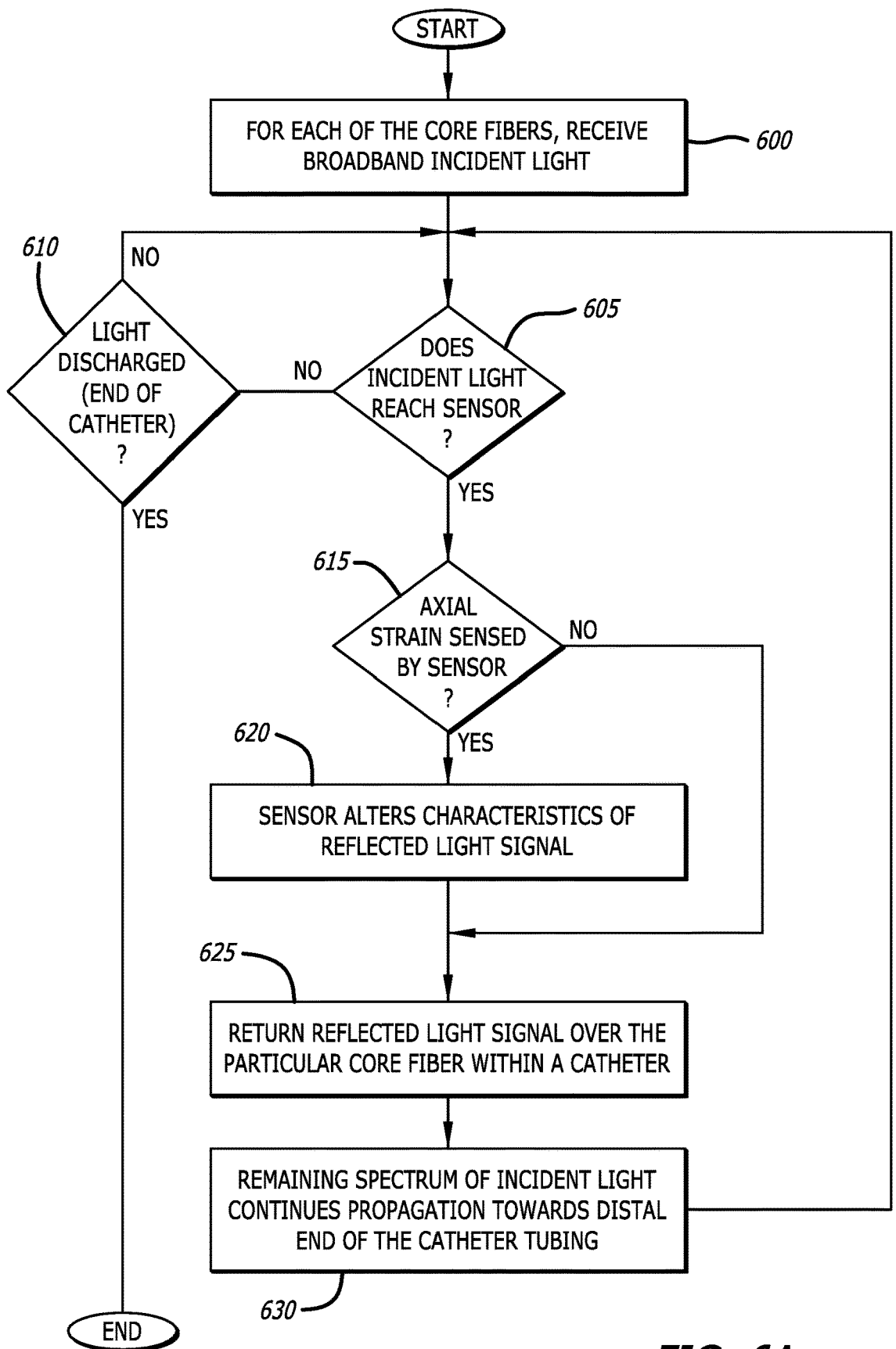
FIGS. 6A-6B are flowcharts of the methods of operations conducted by the medical instrument monitoring system of FIGS. 1A-1B to achieve optic 3D shape sensing in accordance with some embodiments.
Figure 6B:
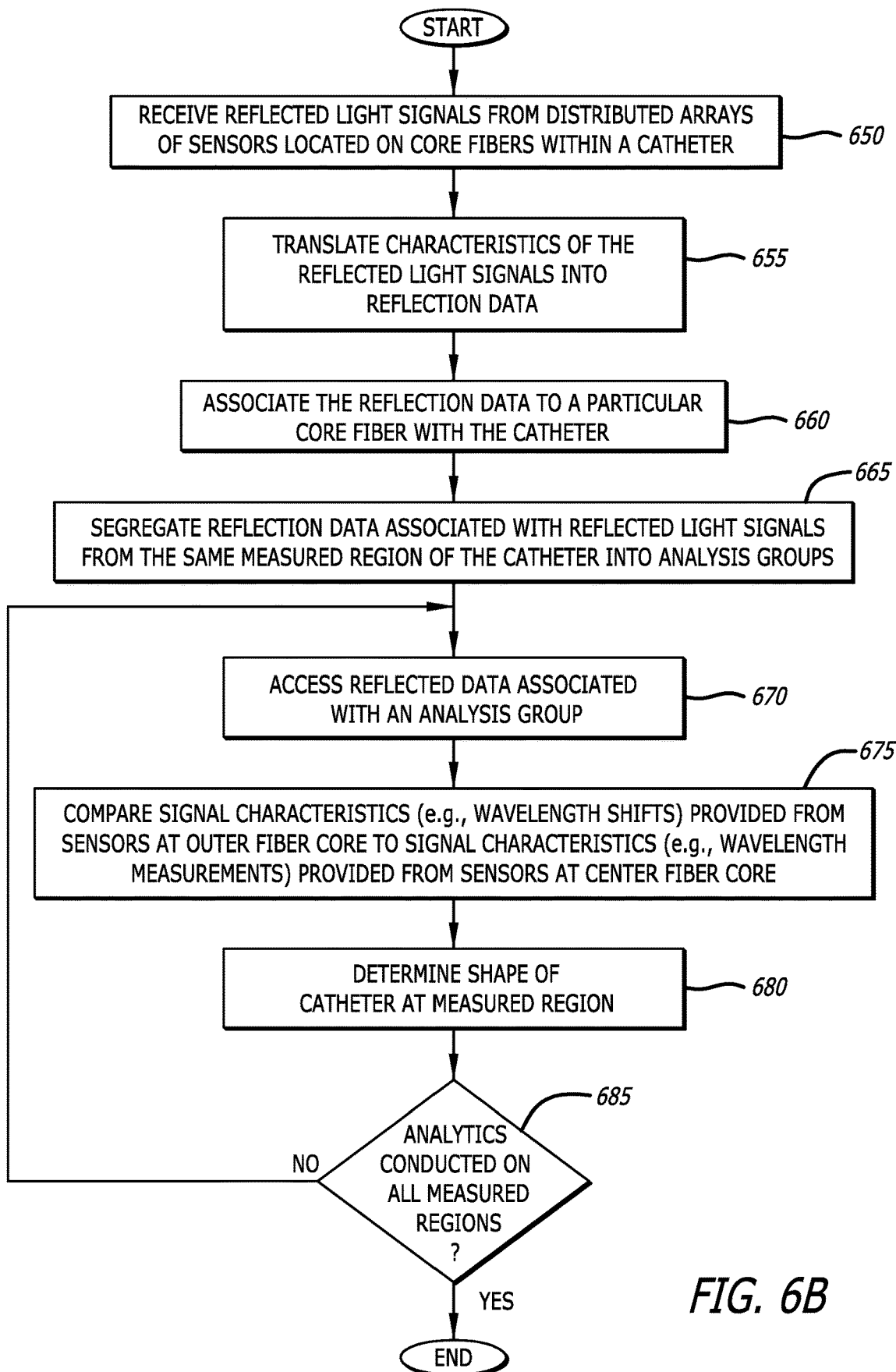

Referring to FIGS. 6A-6B, flowcharts of methods of operations conducted by the medical instrument monitoring system of FIGS. 1A-1B to achieve optic 3D shape sensing are shown in accordance with some embodiments. Herein, the catheter includes at least one septum spanning across a diameter of the tubing wall and continuing longitudinally to subdivide the tubing wall. The medial portion of the septum is fabricated with a first micro-lumen, where the first micro-lumen is coaxial with the central axis of the catheter tubing. The first micro-lumen is configured to retain a center core fiber. Two or more micro-lumen, other than the first micro-lumen, are positioned at different locations circumferentially spaced along the wall of the catheter tubing. For example, two or more of the second plurality of micro-lumens may be positioned at different quadrants along the circumference of the catheter wall.

Furthermore, each core fiber includes a plurality of sensors spatially distributed along its length between at least the proximal and distal ends of the catheter tubing. This array of sensors is distributed to position sensors at different regions of the core fiber to enable distributed measurements of strain throughout the entire length or a selected portion of the catheter tubing. These distributed measurements may be conveyed through reflected light of different spectral widths (e.g., specific wavelength or specific wavelength ranges) that undergoes certain wavelength shifts based on the type and degree of strain.

According to one embodiment of the disclosure, as shown in FIG. 6A, for each core fiber, broadband incident light is supplied to propagate through a particular core fiber (block 600). Unless discharged, upon the incident light reaching a sensor of a distributed array of sensors measuring strain on a particular core fiber, light of a prescribed spectral width associated with the first sensor is to be reflected back to an optical receiver within a console (blocks 605-610). Herein, the sensor alters characteristics of the reflected light signal to identify the type and degree of strain on the particular core fiber as measured by the first sensor (blocks 615-620). According to one embodiment of the disclosure, the alteration in characteristics of the reflected light signal may signify a change (shift) in the wavelength of the reflected light signal from the wavelength of the incident light signal associated with the prescribed spectral width. The sensor returns the reflected light signal over the core fiber and the remaining spectrum of the incident light continues propagation through the core fiber toward a distal end of the catheter tubing (blocks 625-630). The remaining spectrum of the incident light may encounter other sensors of the distributed array of sensors, where each of these sensors would operate as set forth in blocks 605-630 until the last sensor of the distributed array of sensors returns the reflected light signal associated with its assigned spectral width and the remaining spectrum is discharged as illumination.

Referring now to FIG. 6B, during operation, multiple reflected light signals are returned to the console from each of the plurality of core fibers residing within the corresponding plurality of micro-lumens formed within a catheter, such as the catheter of FIG. 1B. In particular, the optical receiver receives reflected light signals from the distributed arrays of sensors located on the center core fiber and the outer core fibers and translates the reflected light signals into reflection data, namely electrical signals representative of the reflected light signals including wavelength shifts caused by strain (blocks 650-655). The reflection data classification logic is configured to identify which core fibers pertain to which reflection data and segregate reflection data provided from reflected light signals pertaining to a particular measurement region (or similar spectral width) into analysis groups (block 660-665).

Each analysis group of reflection data is provided to shape sensing logic for analytics (block 670). Herein, the shape sensing logic compares wavelength shifts at each outer core fiber with the wavelength shift at the center core fiber positioned along central axis and operating as a neutral axis of bending (block 675). From this analytics, on all analytic groups (e.g., reflected light signals from sensors in all or most of the core fibers), the shape sensing logic may determine the shape the core fibers have taken in three-dimensional space, from which the shape sensing logic can determine the current physical state of the catheter in three-dimension space (blocks 680-685).

Figure 7:
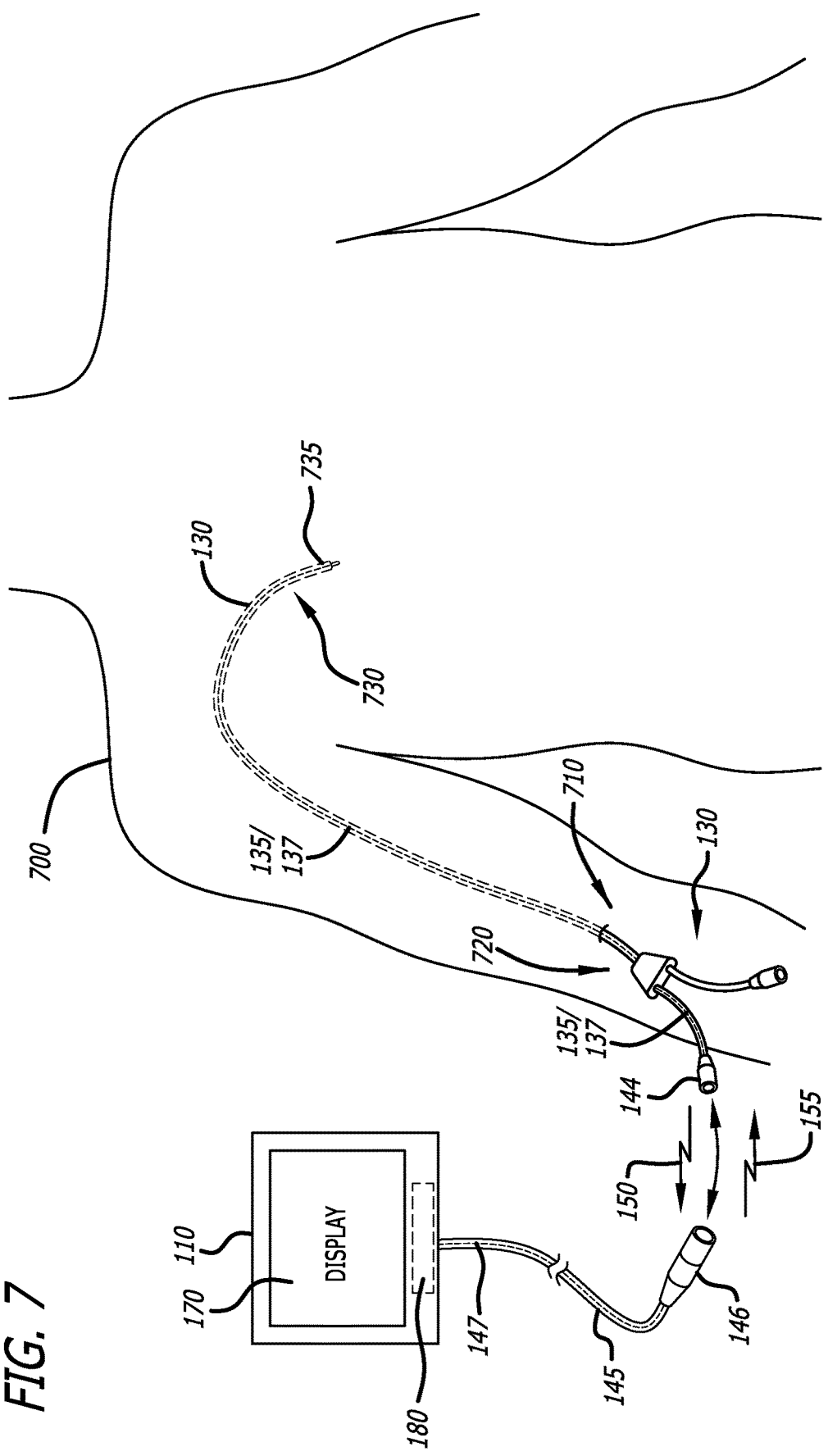
FIG. 7 is an exemplary embodiment of the medical instrument monitoring system of FIGS. 1A-1B during operation and insertion of the catheter into a patient in accordance with some embodiments.

Referring to FIG. 7, an exemplary embodiment of the medical instrument monitoring system of FIG. 1B during operation and insertion of the catheter into a patient are shown in accordance with some embodiments. Herein, the catheter 130 generally includes the integrated tubing of the catheter 130 with a proximal portion 720 that generally remains exterior to the patient 700 and a distal portion 730 that generally resides within the patient vasculature after placement is complete. The (integrated) catheter tubing of the catheter 130 may be advanced to a desired position within the patient vasculature such as a distal end (or tip) 735 of the catheter tubing of the catheter 130 is proximate the patient's heart, such as in the lower one-third (⅓) portion of the Superior Vena Cava ("SVC") for example. In some embodiments, various instruments may be disposed at the distal end 735 of the catheter 130 to measure pressure of blood in a certain heart chamber and in the blood vessels, view an interior of blood vessels, or the like. In alternative embodiments, such as those that utilize the stylet assembly of FIG. 1A and the catheter 195, such instruments may be disposed at a distal end of the stylet 120.

During advancement through a patient vasculature, the catheter tubing of the catheter 130 receives broadband incident light 155 from the console 110 via optical fiber(s) 147 within the interconnect 145, where the incident light 155 propagates along the core fibers 137 of the multi-core optical fiber 135 within the catheter tubing of the catheter 130. According to one embodiment of the disclosure, the connector 146 of the interconnect 145 terminating the optical fiber(s) 147 may be coupled to the optical-based catheter connector 144, which may be configured to terminate the core fibers 137 deployed within the catheter 130. Such coupling optically connects the core fibers 137 of the catheter 130 with the optical fiber(s) 147 within the interconnect 145. The optical connectivity is needed to propagate the incident light 155 to the core fibers 137 and return the reflected light signals 150 to the optical logic 180 within the console 110 over the interconnect 145. As described below in detail, the physical state of the catheter 130 may be ascertained based on analytics of the wavelength shifts of the reflected light signals 150.

Figure 8A:
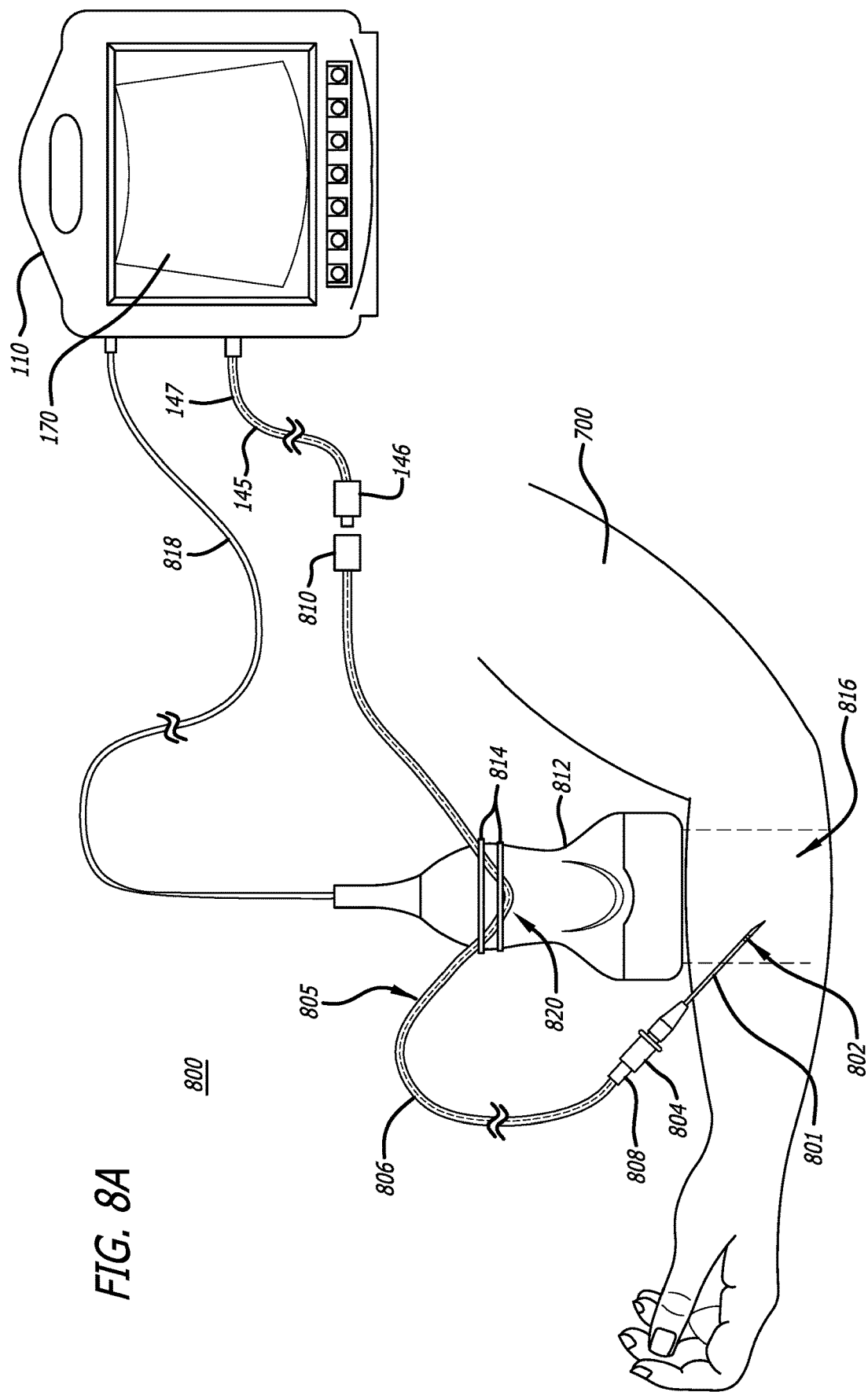
FIG. 8A is an alternative embodiment of the medical instrument monitoring system of FIGS. 1A-1B including an optically-enabled needle during operation in accordance with some embodiments.

Referring now to FIG. 8A, an alternative embodiment of the medical instrument monitoring system of FIGS. 1A-1B including an optically-enabled needle during operation is shown in accordance with some embodiments. Herein, the medical instrument monitoring system 800 includes the optically-enabled needle 801, which includes Bragg fiber gratings 802 at a distal end. For example, the gratings 802 may be integrated directly on an inner wall of the lumen of the needle 801. The gratings 802 provide numerous advantages including the ability to obtain measurements of the consistency of patient tissue (e.g., via strain experienced by the gratings 802 during insertion and advancement toward a blood vessel).

Further, a proximal end of the needle 801 includes a needle-based optical connector 804 that is configured to couple with an optical connector 808 disposed at a distal end of an interconnect 805 which includes an optical fiber 806. The optical fiber 806 may be a multi-core optical fiber and include one or more core fibers $807_1$-$807_P$ (collectively, "core fibers 807" and having the properties and capabilities of the core fibers 137 discussed herein). The optical fiber 806 also includes an optical connector 810 at its proximal end that is configured to couple with the connector 146 interconnect 145, which couples to the console 110. The interconnect 145 houses the optical fiber 147, as noted above. Thus, optical signals, e.g., incident light and reflected light, may be transmitted between the console 110 and the needle 801. The medical instrument monitoring system 800 of FIG. 8A further includes an ultrasound probe 812 configured to obtain ultrasound imaging data of an imaging area 816, where the ultrasound imaging data may be provided to the console 110 via the electrical/ultrasound connection 818.

In particular, in the embodiment illustrated, the optical fiber 806 is coupled (or otherwise secured) to the probe 812 via the securement mechanism 814, which may include one or more straps (e.g., elastic or otherwise) or adhesive strips (e.g., medical tape). The optical fiber 806 is coupled to the probe 812 in such a manner so as to create a bend or kink (referred to herein as "bend 820") in the optical fiber 806. The bend 820 causes a consistent strain on the gratings of a particular section of core fibers 807, thereby providing a consistent wavelength shift of the reflected light. As a result, the shape sensing logic 194 may receive reflected light and detect the positioning along the optical fiber 806 at which point the bend 820 occurs. The shape sensing logic 194 may then utilize the position of the bend 820 as a reference point in determining a positioning, location and/or orientation of the needle 801. In one embodiment, when determining the positioning, location and/or orientation of the needle 801, the bend 820 may serve as a point of origin. Thus, the positioning, location and/or orientation of the needle 801 may be determined with respect to the probe 812.

Thus, the medical instrument monitoring system 800 may obtain ultrasound image data of the imaging area 816 from the probe 812 and additionally determine needle tracking information based on the reflected light. The bend 820 serves as a reference point in determining a positioning of the needle 801, and particularly a distal tip of the needle 801, relative to the probe 812. The needle tracking information may then be displayed as an overlay to the ultrasound image data as displayed on display 170 of the console 110.

Figure 8B:
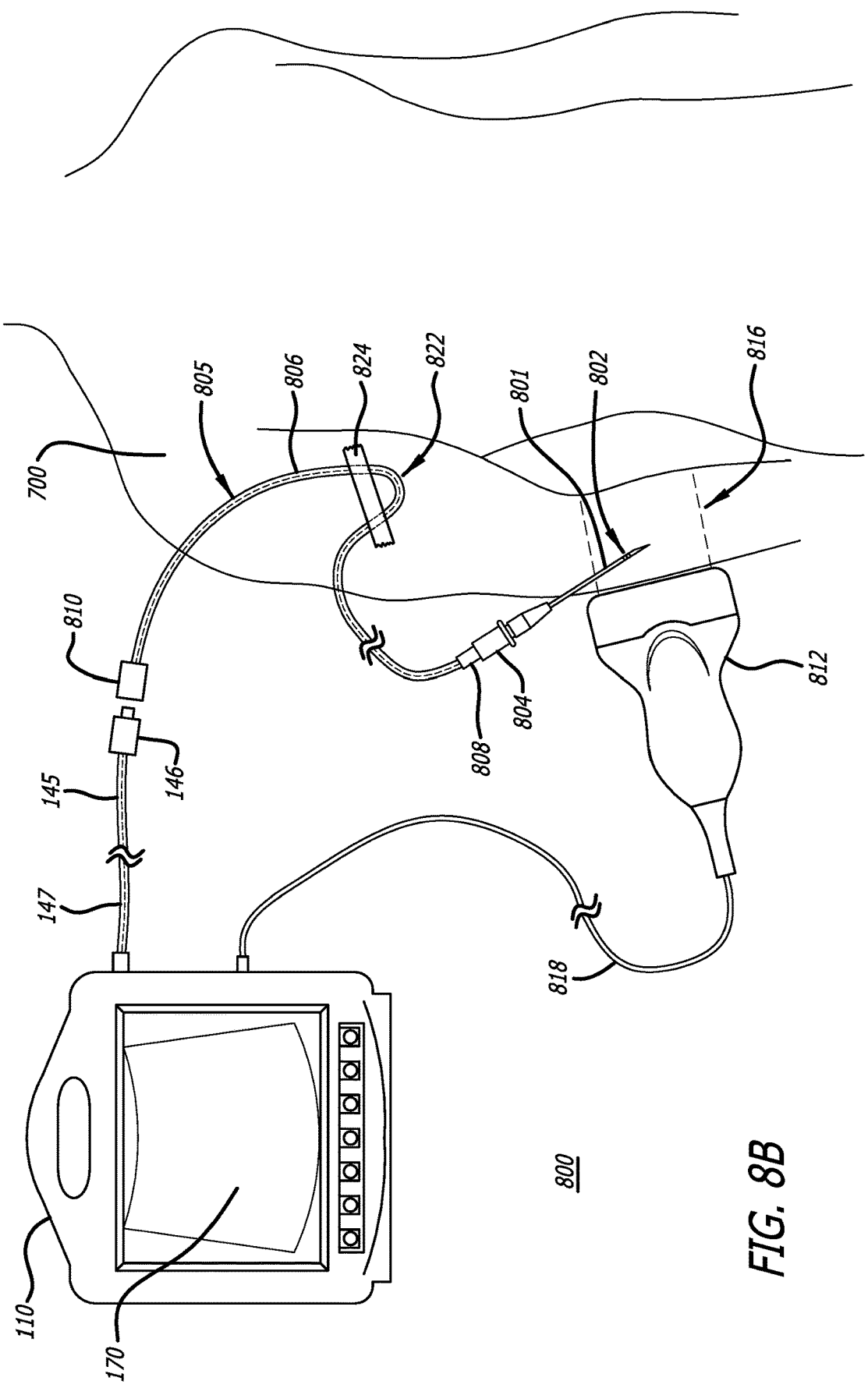
FIG. 8B is a second exemplary embodiment of the medical instrument monitoring system of FIG. 8A during operation in accordance with some embodiments.

Referring to FIG. 8B, a second exemplary embodiment of the medical instrument monitoring system of FIG. 8A during operation is shown in accordance with some embodiments. FIG. 8B illustrates the medical instrument monitoring system 800 including the optically-enabled needle 801 of FIG. 8A, which includes Bragg fiber gratings 802 at a distal end and the needle-based optical connector 804 that is configured to couple with an optical connector 808 of the interconnect 805.

In contrast to the embodiment of FIG. 8A, the embodiment illustrated, in FIG. 8B discloses the interconnect 805 (and thus the core fiber 806) coupled, or otherwise secured, to the patient 700 via a securement mechanism 824, which may include one or more adhesive strips or patches (e.g., medical tape, etc.) or adjustable straps. The interconnect 805 is coupled to the patient 700 in such a manner so as to create a bend or kink (referred to herein as "bend 822") in the optical fiber 806. Like the bend 820 of FIG. 8A, the bend 822 causes a consistent strain on the gratings of a particular section of core fibers 807, which provides a consistent wavelength shift of the reflected light. As a result, the shape sensing logic 194 may receive reflected light and detect the positioning along the optical fiber 806 at which point the bend 822 occurs and can further utilize the position of the bend 822 as a reference point in determining a positioning, location and/or orientation of the needle 801.

Thus, medical instrument monitoring system 100 may obtain ultrasound image data of the imaging area 816 from the probe 812 and additionally determine needle tracking information based on the reflected light. The bend 822 serves as a reference point in determining a positioning of the needle 801, and particularly a distal tip of the needle 801, relative to the patient 700. The needle tracking information may then be displayed as an overlay to the ultrasound image data as displayed on display 170 of the console 110.

Figure 8C:
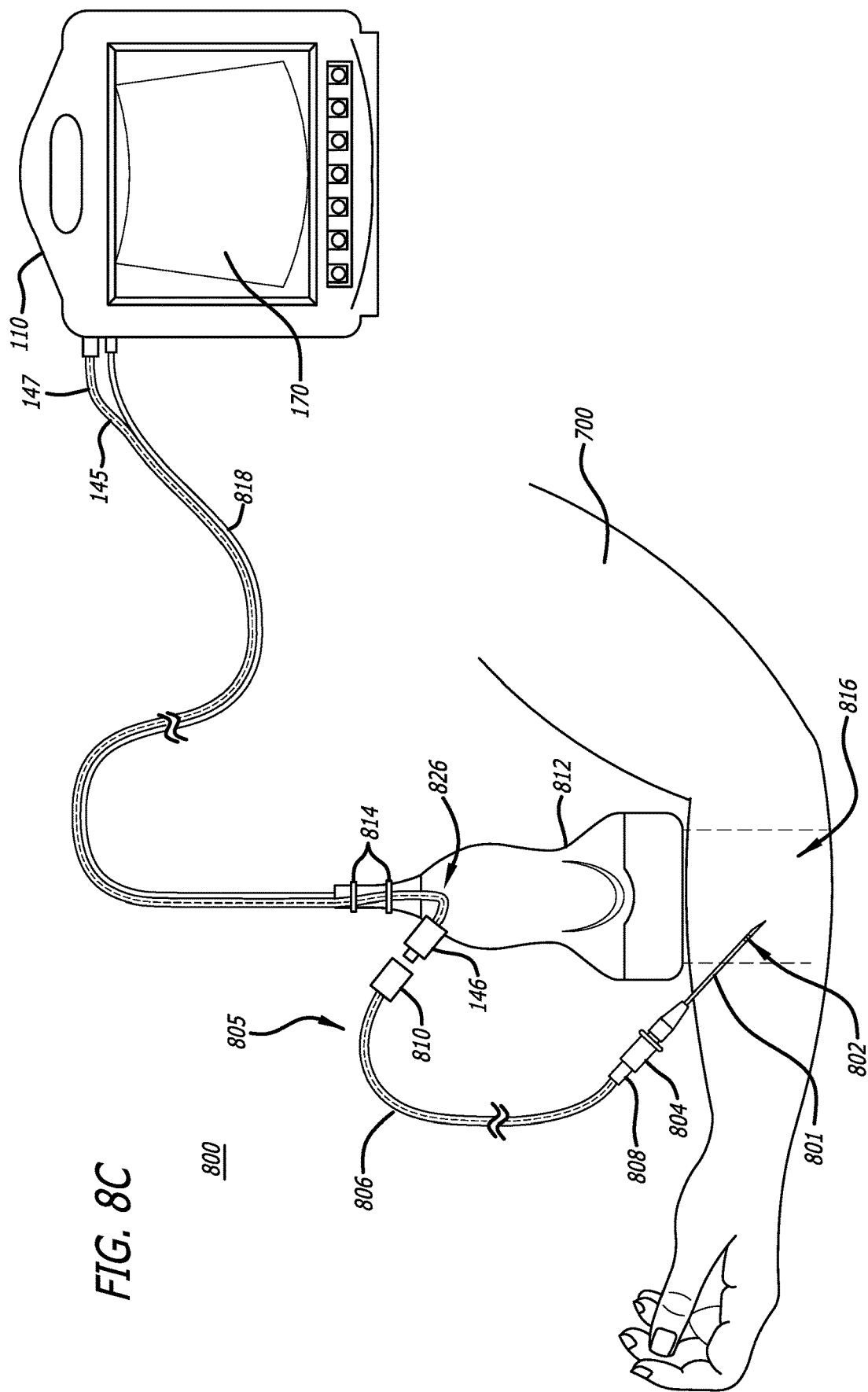
FIG. 8C is a third exemplary embodiment of the medical instrument monitoring system of FIG. 8A during operation in accordance with some embodiments.

Referring now to FIG. 8C, a third exemplary embodiment of the medical instrument monitoring system of FIG. 8A during operation is shown in accordance with some embodiments. The embodiment of FIG. 8C illustrates that the interconnect 145 may include a predetermined bend 826 at its distal end. Further, the interconnect 145 may be coupled (or otherwise secured) to the probe 812 via the securement mechanism 814, as discussed above. In some embodiments, the interconnect 145 may be manufactured with the predetermined bend 826 as shown in FIG. 8C. However, as shown in other embodiments, a predetermined bend may be formed as a result of the coupling of an interconnect to the probe 812 or patient 700. Further, FIG. 8C illustrates that at least a length of the interconnect 145 be may collocated with the electrical/ultrasound connection 818.

Figure 9A:
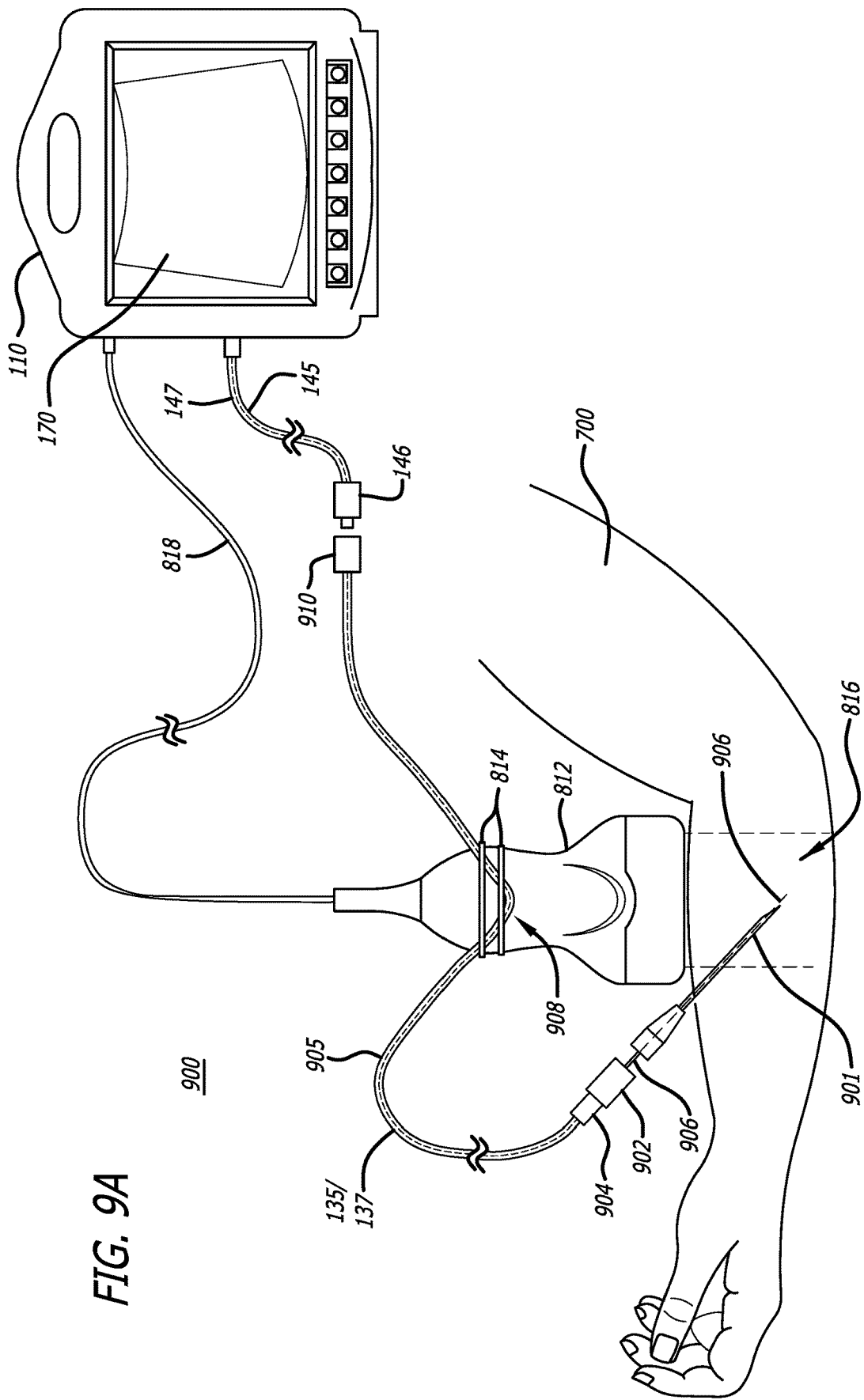
FIG. 9A is a second alternative embodiment of the medical instrument monitoring system of FIGS. 1A-1B including an optically-enabled stylet within a needle during operation in accordance with some embodiments.

Referring now to FIG. 9A, a second alternative embodiment of the medical instrument monitoring system of FIGS. 1A-1B including an optically-enabled stylet within a needle during operation is shown in accordance with some embodiments. Herein, the medical instrument monitoring system 900 includes a needle 901 one or more lumens, within which a stylet 906 is disposed.

The stylet 906 may be a component of a stylet assembly that is may be similar in form to and perform similar functionalities as the stylet assembly 119 discussed above. For instance, the stylet 906 may be similar in form to and perform similar functionalities as the stylet 120. In particular, the stylet 906 may include an optical fiber 135 having core fibers 137 disposed therein, such that the physical state of the stylet 906 may be based on changes in characteristics of reflected light signals 150 received at the console from the optical fiber of stylet 906. The characteristics may include shifts in wavelength caused by strain on certain regions of the core fibers integrated within an optical fiber core 135 positioned within the stylet 906. From information associated with the reflected light signals 150, the console 110 may determine (through computation or extrapolation of the wavelength shifts) the physical state, such as positioning, location and orientation, of the stylet 906.

Further, the interconnect 905 may also include an optical fiber 135 having core fibers 137 that propagate incident light and reflected light signals. The core fibers 137 of the interconnect 905 may also include Bragg fiber gratings 802, which also cause reflected light signals 150 to be returned to the console 110. The stylet 906 may include an optical connector 902 at its proximal end that is configured to optically couple with an optical connector 904 located at a distal end of the interconnect 905. Additionally, a proximal end of the interconnect includes an optical connector 910 that is configured to optically couple with the connector 146 of the interconnect 145. Thus, incident light 150 may propagate from the console 110 to the distal end of the stylet 906 and reflected light signals may propagate in the opposite direction to be received by the console 110.

In particular, in the embodiment illustrated, the interconnect 905 is coupled (or otherwise secured) to the probe 812 via the securement mechanism 814. The interconnect 905 is coupled to the probe 812 in such a manner so as to create a bend or kink (referred to herein as "bend 908") in the interconnect 905. The bend 908 causes a consistent strain on the gratings strain on the gratings of a particular section of core fibers 137 of the interconnect 905 and thus provides a consistent wavelength shift of the reflected light. As a result, the shape sensing logic 194 may receive reflected light and detect the positioning along the optical fiber 135 at which point the bend 908 occurs. The shape sensing logic 194 then utilizes the position of the bend 908 as a reference point in determining a positioning, location and/or orientation of the stylet 906, and also that of a needle 901 configured to receive the stylet 906.

Thus, medical instrument monitoring system 900 may obtain ultrasound image data of the imaging area 816 from the probe 812 and additionally determine needle tracking information based on the reflected light. The bend 908 serves as a reference point in determining a positioning of the stylet 906 (and of the needle 901) relative to the probe 812. The needle tracking information may then be displayed as an overlay to the ultrasound image data as displayed on display 170 of the console 110.

Figure 9B:
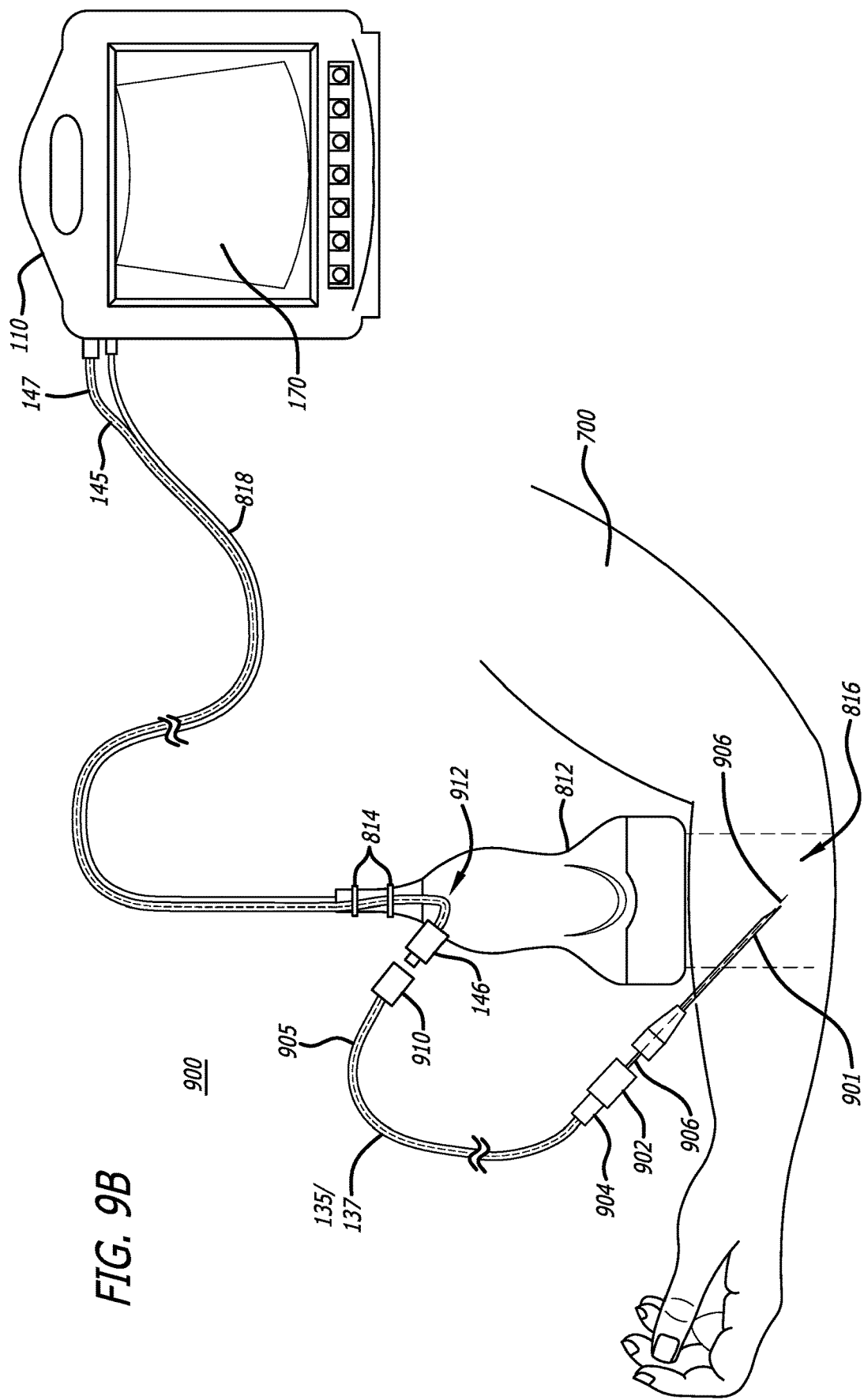
FIG. 9B is a second exemplary embodiment of the medical instrument monitoring system of FIG. 9A during operation in accordance with some embodiments.

Referring now to FIG. 9B, second exemplary embodiment of the medical instrument monitoring system of FIG. 9A during operation is shown in accordance with some embodiments. The embodiment of FIG. 9B illustrates that the interconnect 145 may include a predetermined bend 912 at its distal end. Further, the interconnect 145 may be coupled (or otherwise secured) to the probe 812 via the securement mechanism 814, as discussed above.

Figure 10:
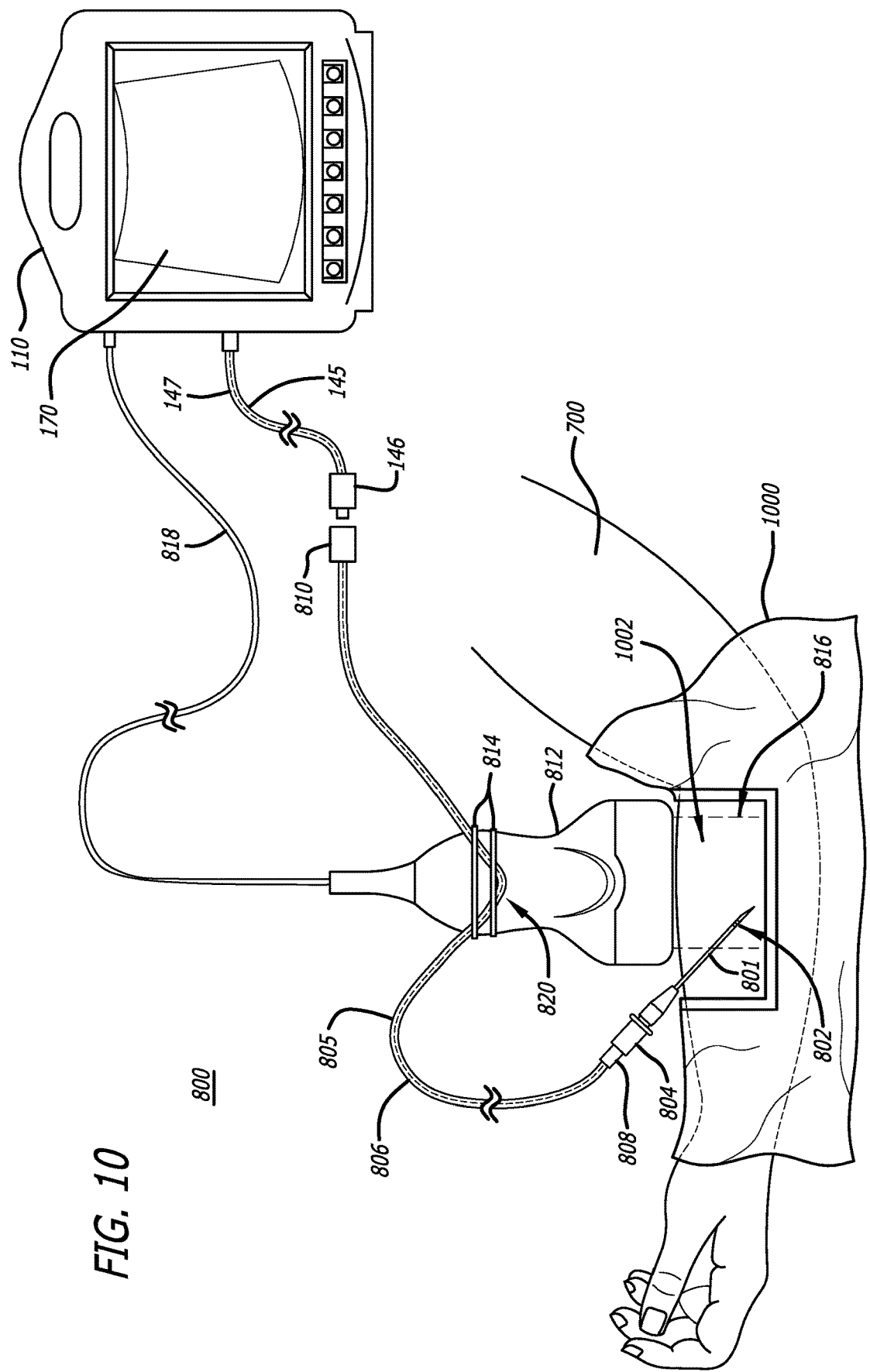
FIG. 10 is an illustration of the medical instrument monitoring system of FIG. 8A including a sterile drape during operation in accordance with some embodiments.

Referring to FIG. 10, an illustration of the medical instrument monitoring system of FIG. 8A including a sterile drape during operation is shown in accordance with some embodiments. FIG. 10 illustrates the medical instrument monitoring system 800 in operation where the imaging area 816 is within a sterile area 1002 that is located within the opening of the sterile drape 1000.

Figure 11:
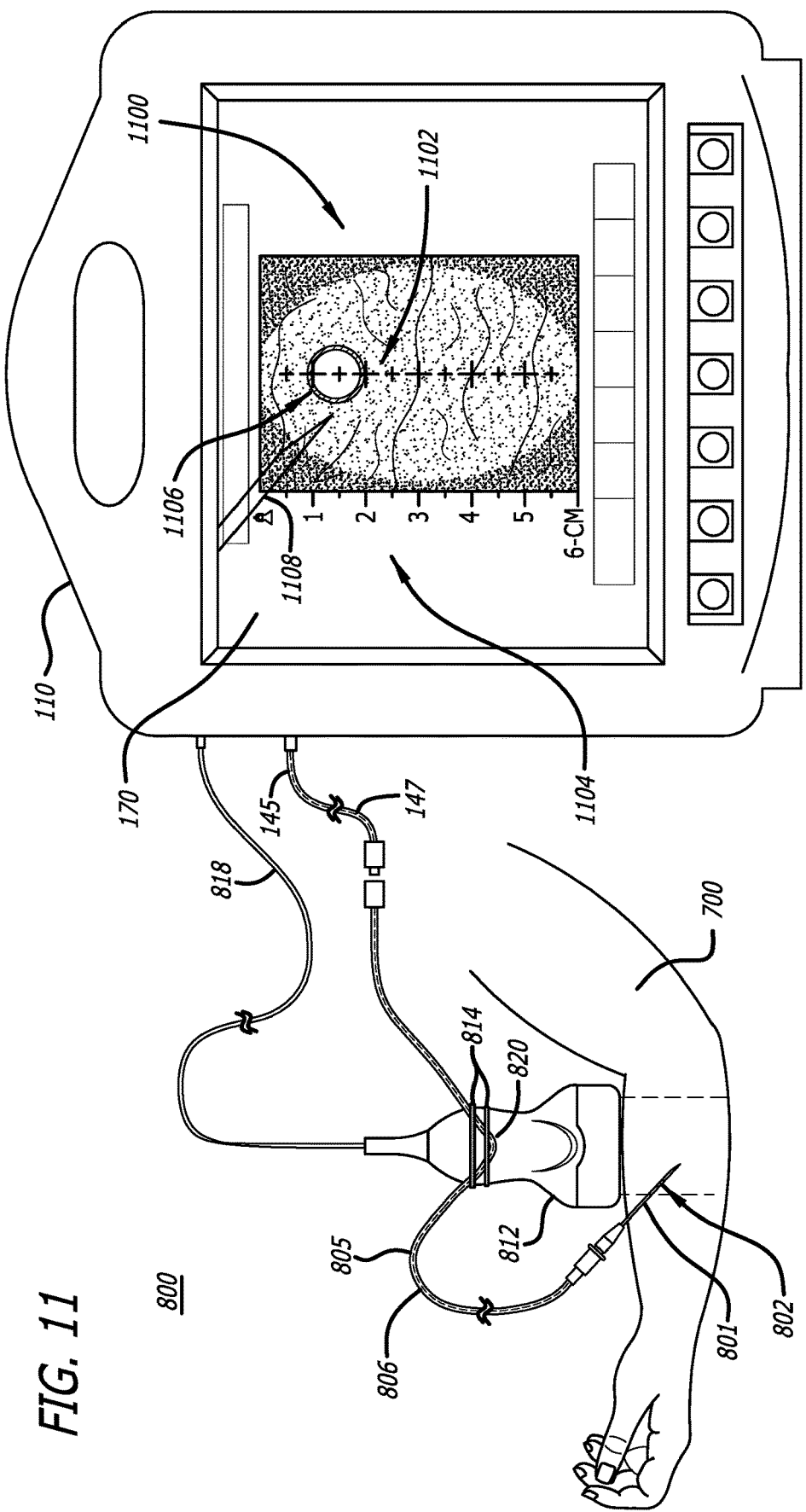
FIG. 11 is an illustration of the medical instrument monitoring system of FIG. 8A during use including an exemplary visualization rendered on a display in accordance with some embodiments.

Referring now to FIG. 11, an illustration of the medical instrument monitoring system of FIG. 8A during use including an exemplary visualization rendered on a display is shown in accordance with some embodiments. FIG. 11 illustrates the medical instrument monitoring system 800 in operation and specifically illustrates the rendering of an ultrasound image 1100 and an image of the needle 801 as an overlay. The ultrasound image 1100 may include depth markers 1102, an image depth scale 1104 and an image of a target vessel 1106.

The shape sensing logic 194 generates the overlay 1108 by processing the reflected received from the from the gratings 802 of the needle 801 and gratings disposed along the length of the optical fiber 806 and specifically along the one or more core fibers 807. Specifically, the physical state of the needle 801 and interconnect 805 are ascertained based on analytics of the wavelength shifts of the reflected light. Additionally, as the bend 820 causes a known wavelength shift of the light reflected from the corresponding portion of the interconnect 805, the positioning and orientation of the needle 801 are determined relative to the bend 820. Thus, the location of the distal tip of the needle 801 may be ascertained relative to the imaging area 816. As a result, the shape sensing logic 194 may generate the overlay 1108, e.g., an image of the needle 801 with its position and orientation relative to the ultrasound image 1100.

Figure 12:
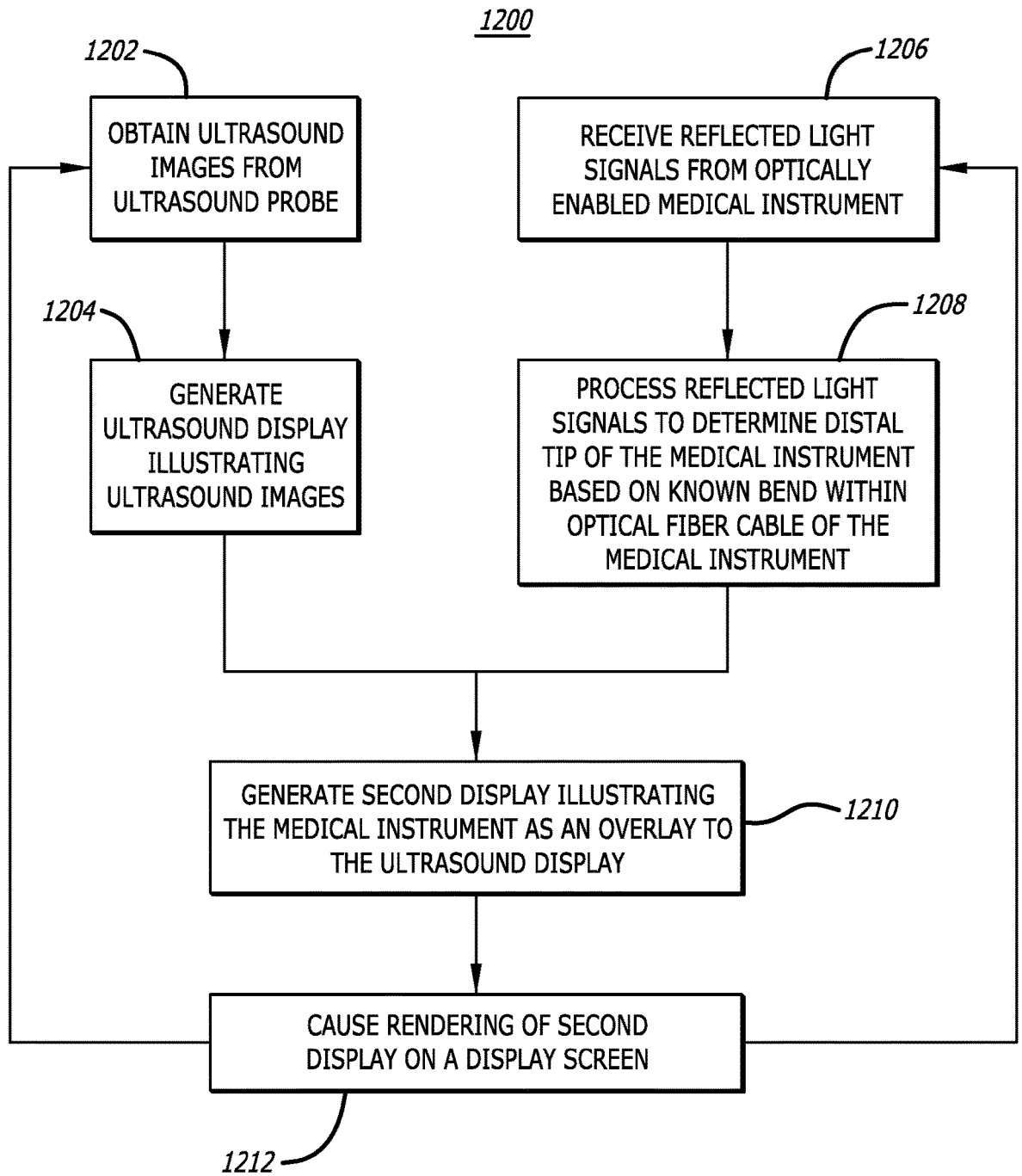
FIG. 12 is a flowchart of an exemplary methodology of inserting a medical instrument into a patient vasculature in accordance with some embodiments.

Referring to FIG. 12, a flowchart of an exemplary methodology of inserting a medical instrument into a patient vasculature is shown in accordance with some embodiments. Each block illustrated in FIG. 12 represents an operation performed in the method 1200, which is initiated when the medical instrument monitoring system of any of FIGS. 8A-11 are deployed to insert a medical instrument into a patient vasculature. Thus, the medical instrument may be either of the optically-enabled needle of FIG. 8A or the catheter assembly of FIG. 9A. According to one embodiment, the method 1200 includes obtaining ultrasound images from an ultrasound probe and generating an ultrasound display illustrating one or more ultrasound images (blocks 1202-1204). Additionally, and occurring either prior to, following, or concurrently (at least partially overlapping in time) and either serially or in parallel, the method 1200 includes receiving reflect light signals from an optically-enabled medical instrument and processing the reflected light signals to determine a positioning and orientation of a distal tip of the medical instrument based on a known bend within an optical fiber cable coupled to the medical instrument (blocks 1206-1028).

Upon receiving the ultrasound images and the reflected light signals, and processing each accordingly, the method 1200 includes generating a second display illustrating the medical instrument as an overlay to the ultrasound display 1210 (block 1210). A shape sensing logic of the console that received the ultrasound images and the reflected light signals may perform processing to determine a positioning and an orientation of the medical instrument relative to the known bend of the optical fiber cable. In particular, the positioning and orientation of a distal tip of the medical instrument may be determined such that the distal tip may be included within the overlay, when applicable, in order to provide the clinician inserting the medical instrument within a patient a visual indication as to the positioning of the distal tip relative to a target vessel. Following generation of the second display illustrating the medical instrument as an overlay to the ultrasound display, the method 1200 includes rendering, or causing the rendering, of the second display on a display screen (block 1212).

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A medical instrument system for inserting a medical instrument within a patient body, the system comprising:
   the medical instrument comprising a first optical fiber having one or more core fibers;
   an interconnect including a second optical fiber having one or more core fibers, the second optical fiber extending along a length of the interconnect, wherein:
      a distal end of the second optical fiber is optically coupled with a proximal end of the first optical fiber, and
      a predetermined bend is formed in the interconnect including the second optical fiber at a point along the length of the interconnect; and
   a console optically coupled to a proximal end of the interconnect including the second optical fiber, the console including one or more processors and a non-transitory computer-readable medium having stored thereon logic, when executed by the one or more processors, causes operations including:
      providing an incident light signal to the first optical fiber and the second optical fiber,
      receiving reflected light signals of different spectral widths of the incident light signal from the first optical fiber and the second optical fiber,
      processing the reflected light signals to determine a positioning and an orientation of the medical instrument relative to the predetermined bend,
      generating a display of the medical instrument based on the reflected light signals and the determination of the positioning and the orientation of the medical instrument relative to the predetermined bend, and
      causing rendering of the display of the medical instrument on a display screen.

2. The system of claim 1, wherein the medical instrument includes a stylet.

3. The system of claim 2, wherein the medical instrument further includes a needle, and wherein the stylet is disposed within a lumen of the needle.

4. The system of claim 1, further comprising an ultrasound probe coupled to the console, wherein the interconnect is coupled to the ultrasound probe causing the predetermined bend in the interconnect such that the positioning and the orientation of the medical instrument is determined relative to the ultrasound probe.

5. The system of claim 4, wherein the logic, when executed by the one or more processors, causes further operations including:
   receiving ultrasound imaging data from the ultrasound probe, and
   causing rendering of an ultrasound image from the ultrasound imaging data, wherein the display of the medical instrument is rendered as an overlay on the ultrasound image.

6. The system of claim 1, wherein the interconnect is coupled to the patient body causing the predetermined bend in the interconnect such that the positioning and the orientation of the medical instrument is determined relative to the patient body.

7. The system of claim 1, wherein each of the one or more core fibers of the first optical fiber and the second optical fiber includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of a corresponding optical fiber.

8. The system of claim 1, wherein the first optical fiber and the second optical fiber are single-core optical fibers, and wherein the incident light signal is provided in pulses.

9. The system of claim 1, wherein the first optical fiber and the second optical fiber are multi-core optical fibers, each including a plurality of core fibers.

10. The system of claim 1, wherein the medical instrument is one of an introducer wire, a guidewire, a needle with the first optical fiber inlayed into a cannula of the needle, or a catheter with the first optical fiber inlayed into one or more walls of the catheter.

11. A medical instrument system for inserting a medical instrument within a patient body, the system comprising:
    the medical instrument comprising a first optical fiber having one or more core fibers;
    an interconnect including a second optical fiber having one or more core fibers, the second optical fiber extending along a length of the interconnect, wherein a distal end of the interconnect including the second optical fiber is optically coupled with a proximal end of the medical instrument including the first optical fiber, and wherein a portion of the interconnect includes a predetermined bend; and
    a console optically coupled to the medical instrument, a proximal end of the interconnect including the second optical fiber optically coupled to the console, the console including one or more processors and a non-transitory computer-readable medium having stored thereon logic, when executed by the one or more processors, causes operations including:
       providing an incident light signal to the first optical fiber,
       receiving reflected light signals of different spectral widths of the incident light signal from the first optical fiber,
       processing the reflected light signals to determine a positioning and an orientation of the medical instrument,
       generating a display of the medical instrument based on the reflected light signals and the determination of the positioning and the orientation of the medical instrument, and
       causing rendering of the display of the medical instrument on a display screen.

12. The system of claim 11, wherein the incident light signal and the reflected light signals are transmitted between the console and the medical instrument via the interconnect.

13. The system of claim 11, further comprising an ultrasound probe coupled to the console via an ultrasound connection, wherein the portion of the interconnect that includes the predetermined bend is coupled to the ultrasound probe.

14. The system of claim 13, wherein the length of the interconnect is collocated with the ultrasound connection.

15. The system of claim 13, wherein determination of the positioning and the orientation of the medical instrument is relative to the predetermined bend.

16. A medical instrument system for inserting a medical instrument within a patient body, the system comprising:
    the medical instrument comprising a first optical fiber having one or more core fibers;

an interconnect including a second optical fiber having one or more core fibers, the second optical fiber extending along a length of the interconnect, where a distal end of the interconnect including the second optical fiber is optically coupled with a proximal end of the medical instrument including the first optical fiber;

a console optically coupled to the medical instrument, a proximal end of the interconnect including the second optical fiber optically coupled to the console, the console including one or more processors and a non-transitory computer-readable medium having stored thereon logic, when executed by the one or more processors, causes operations including:

provuding an incident light signal to the first optical fiber, receiving reflected light signals of different spectral widths of the incident light signal from the first optical fiber, processing the reflected light signals to determine a positioning and an orientation of the medical instrument, generating a display of the medical instrument based on the reflected light signals and the determination of the positioning and the orientation of the medical instrument, and causing rendering of the display of the medical instrument on a display screen; and an ultrasound probe coupled to the console via an ultrasound connection, wherein a portion of the interconnect that includes a predetermined bend is coupled to the ultrasound probe.

17. The system of claim 16, wherein the incident light signal and the reflected light signals are transmitted between the console and the medical instrument via the interconnect.

18. The system of claim 16, wherein the length of the interconnect is collocated with the ultrasound connection.

19. The system of claim 16, wherein determination of the positioning and the orientation of the medical instrument is relative to the predetermined bend.

* * * * *